United States Patent
Paufique

(10) Patent No.: US 10,987,297 B2
(45) Date of Patent: *Apr. 27, 2021

(54) **COSMETIC AGENT FORMED BY GALACTOMANNANS OBTAINED FROM *CAESALPINIA SPINOSA* AND CROSS-LINKED SULPHATED GALACTANS OBTAINED FROM *KAPPAPHYCUS ALVAREZII***

(71) Applicant: Societe Industrielle Limousine D'Application Biologique, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

( * ) Notice: Subject to any disclaimer, the term of this patent is extended or adjusted under 35 U.S.C. 154(b) by 28 days.

This patent is subject to a terminal disclaimer.

(21) Appl. No.: 16/072,261

(22) PCT Filed: Jan. 27, 2017

(86) PCT No.: PCT/EP2017/051827
§ 371 (c)(1),
(2) Date: Jul. 24, 2018

(87) PCT Pub. No.: WO2017/129780
PCT Pub. Date: Aug. 3, 2017

(65) Prior Publication Data
US 2019/0070093 A1 Mar. 7, 2019

(30) Foreign Application Priority Data

Jan. 29, 2016 (FR) ...................................... 1650741

(51) Int. Cl.
*A61K 8/73* (2006.01)
*A61K 8/9717* (2017.01)
(Continued)

(52) U.S. Cl.
CPC ............... *A61K 8/737* (2013.01); *A61K 8/73* (2013.01); *A61K 8/9717* (2017.08);
(Continued)

(58) Field of Classification Search
None
See application file for complete search history.

(56) References Cited

U.S. PATENT DOCUMENTS

| 4,661,475 A | * | 4/1987 | Bayerlein | ............. A23L 29/238 514/54 |
| 2002/0076769 A1 | * | 6/2002 | Brady | ................. C08B 37/0087 435/101 |

(Continued)

FOREIGN PATENT DOCUMENTS

| EP | 0730867 A2 | 9/1996 |
| FR | 2881349 A1 | 8/2006 |

(Continued)

OTHER PUBLICATIONS

Suiry, et al., "*Kappaphycus alvarezii* (Doty) Doty ex P.C.Silva", AlgaeBase, Feb. 26, 2013, pp. 1-4.
(Continued)

*Primary Examiner* — Dominic Lazaro
(74) *Attorney, Agent, or Firm* — Greer, Burns & Crain, Ltd.

(57) ABSTRACT

A cosmetic or dermocosmetic agent consisting of galactomannans with molecular masses in a range from 1 to 150 kDa obtained from *Caesalpinia spinose* and cross-linked sulfated galactans with molar masses in a range from 1 to 150 kDa obtained from *Kappaphycus alvarezii*. Non-therapeutic cosmetic methods in which the agent is applied on the skin in order to tens the skin and/or to form a film on the skin.

20 Claims, 11 Drawing Sheets

(51) Int. Cl.
    *A61K 8/9789*     (2017.01)
    *A61Q 19/08*     (2006.01)
    *A61Q 17/00*     (2006.01)
    *A61K 36/04*     (2006.01)
    *A61K 36/48*     (2006.01)
    *A61K 9/00*     (2006.01)
    *A61P 39/00*     (2006.01)
    *A61K 8/9794*     (2017.01)

(52) U.S. Cl.
    CPC .......... *A61K 8/9789* (2017.08); *A61K 8/9794* (2017.08); *A61K 9/0014* (2013.01); *A61K 36/04* (2013.01); *A61K 36/48* (2013.01); *A61P 39/00* (2018.01); *A61Q 17/00* (2013.01); *A61Q 19/08* (2013.01); *A61K 2800/95* (2013.01)

(56) References Cited

U.S. PATENT DOCUMENTS

2005/0137272 A1* 6/2005 Gaserod .................. C08L 5/04
    521/50

2006/0182824 A1   8/2006 Lucas et al.
2006/0188465 A1* 8/2006 Perrier .................... A61K 8/73
    424/70.13
2015/0025036 A1   1/2015 Paufique

FOREIGN PATENT DOCUMENTS

| | | |
|---|---|---|
| FR | 2882366 A1 | 8/2006 |
| FR | 2986430 A1 | 8/2013 |
| FR | 3018448 A1 | 9/2015 |
| WO | WO8404039 A1 | 10/1984 |
| WO | WO9819663 A1 | 5/1998 |

OTHER PUBLICATIONS

Laboratorium Kosmetyczne Floslek, "Dermal Filler Day Cream SPF 15", Feb. 5, 2014, pp. 1-4, XP002759145.

Nazca Cosmetics, Leave-in Cream, Mintel, Nov. 1, 2009, pp. 1-3, XP002759146.

Hydromanil, Jan. 1, 2005, pp. 1-17, XP055115308.

* cited by examiner

X-axis: within 0, 5, 10, 15, 20, 25, 30, 35 mU
Y-axis: within...entre 0, 200, 400, 600, 800, 1000, 1200, 1400 nRU X-axis: within...0, 5, 10, 15, 20, 25, 30, 35 mU
Y-axis: within...-1000, 0, 1000, 2000, 3000, 4000, 5000, 6000, 7000 nRU X-axis: within..... 0, 5, 10, 15, 20, 25, 30, 35 mU Y-axis: within...0, 2000, 4000, 6000, 8000, 10000, 12000, 14000, 16000 nRU Efficacy ++++

Efficacy +++

Efficacy ++

Efficacy +

Efficacy -

COSMETIC AGENT FORMED BY GALACTOMANNANS OBTAINED FROM *CAESALPINIA SPINOSA* AND CROSS-LINKED SULPHATED GALACTANS OBTAINED FROM *KAPPAPHYCUS ALVAREZII*

CROSS-REFERENCE TO RELATED APPLICATIONS

This application is a 371 US national stage application of PCT/EP2017/051827 filed Jan. 27, 2017 and claiming a benefit of priority from French patent application FR 1650741 filed Jan. 29, 2016, the entire disclosures of both applications are herein incorporated by reference.

THE TECHNICAL FIELD

The present invention concerns a particular cosmetic agent formed by galactomannans obtained from *Caesalpinia spinosa* and cross-linked sulfated galactans obtained from *Kappaphycus alvarezii*, having a tensor and/or filmogenic effect, and its use for cosmetic or dermocosmetic applications.

BACKGROUND

Women are on a perpetual quest for solutions aimed at keeping their skin young and healthy. They are looking for a product capable of eradicating the signs of time and providing them with protection from the harmful effects of an ever more-aggressive environment. In fact, due to the industrialization and expansion of towns, individuals are regularly exposed to allergens, irritating molecules or fine particles. The latter, particularly emitted by vehicles, have devastating effects on health. Apart from their impact on a respiratory level, they cause major damage to the skin whilst accelerating its ageing: appearance of wrinkles and pigment spots, sagging skin, loss of elasticity and lack of radiance. Faced with this problem, the cosmetics market offers a wide range of anti-ageing and protective treatments. These include products aimed at fundamentally reshaping the skin over the long term in order to restore its youthful appearance. Moreover, an array of anti-oxidants, detoxifiers or stimulators of the natural defenses is available to help the skin protect itself. However, in addition to these "long term" treatments, consumers also want immediate results. Nowadays, treatments very widely include lifting active ingredients capable of instantly improving the signs of ageing. Since 2010, progress in skincare has taken the form of a new category of active ingredients: the "second skin" active ingredients. Having a short- and long-term action, these ingredients are included due to their radiance boost and protective action against external aggressions.

SUMMARY

The aim of the present invention is to propose a new cosmetic agent with a perceptible tensor effect and a lifting and protective film effect boosting youthful skin.

To this end, the invention concerns a cosmetic or dermocosmetic agent formed by the association of specific biopolymers, galactomannans obtained from *Caesalpinia spinosa* with molar masses of between 1 and 150 kDa, and cross-linked sulfated galactans obtained from *Kappaphycus alvarezii* with molar masses of between 1 and 150 kDa.

Galactomannans are known as being emulsifiers, thickeners widely used in cosmetics and foodstuffs. They are very large-sized polysaccharides (around 3000 kDA). The viscosity of these polysaccharides is proportional to the size of the polysaccharides and it provides the thickening effect. There are also some compositions that use a combination of *Caesalpinia spinosa* gum and *Caesalpinia spinosa* oligosaccharides, marketed under the brand name Hydromanil. All of these known products are different from the agent according to the invention and have no tensor and filmogenic efficacy.

In the prior art, kappa carrageenans, containing sulfated galactans, are known as being emulsifiers, thickeners widely used in cosmetics and foodstuffs. They are very large-sized polysaccharides (up to 20000 kDa).

The viscosity of these polysaccharides is proportional to the size of the polysaccharides and has a thickening effect. Cosmetic ingredients can also be found that result from the hydrolysis of *Kappaphycus alvarezii*, like the product described in application FR2986430.

The present invention concerns the association of galactomannans obtained from *Caesalpinia spinosa*, preferably with an average molar mass of between 5 and 30 kDa, and cross-linked sulfated galactans obtained from *Kappaphycus alvarezii*, preferably with an average molar mass of between 5 and 25 kDa. Advantageously, the agent according to the invention has powerful biomechanical and filmogenic properties that confer an efficacy of protective second skin.

Advantageously, they are made without using chemical agents and meet ecodesign requirements. With this particular association of biopolymers, the skin is protected and gains radiance and attractiveness. The visible signs of skin ageing are instantly erased. With this particular association of biopolymers, the skin is protected from pollutants, irritants, allergens and heavy metals. The natural cutaneous barrier of the skin is reinforced because it reduces the penetration of these toxic molecules.

The subject-matter of the invention therefore also concerns the cosmetic use of this cosmetic agent.

The invention also relates to cosmetic compositions that include the cosmetic agent according to the invention as well as to a method of cosmetic treatment of the skin using these compositions.

Further features and advantages will emerge from the following detailed description of the invention with regard to the accompanying Figures.

DEFINITIONS

Figure 1A:
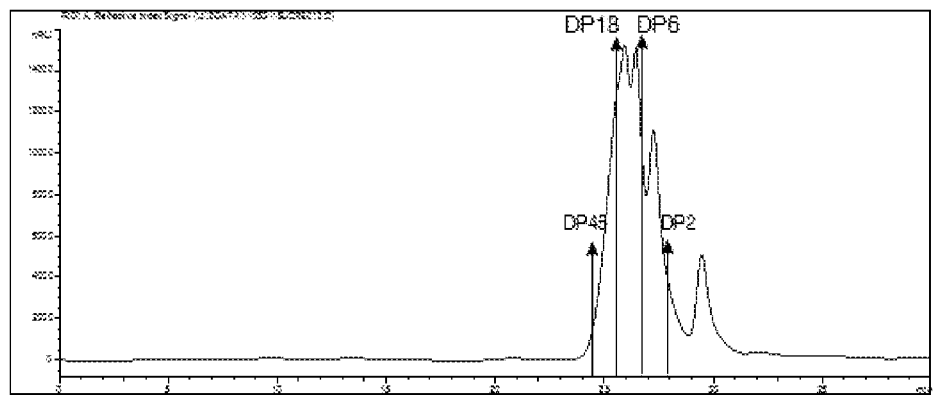
FIG. 1A represents the chromatogram of the product described in application FR2986430.

Within the meaning of the invention, "cosmetic or dermocosmetic agent", also known as "agent", means an active ingredient with a cosmetic effect suitable for topical use in a cosmetic or dermocosmetic composition.

The agent according to the invention consists of biopolymers, and can also be described in the present application by the term "biopolymer".

Within the meaning of the invention, "biopolymers" mean polymers originating from plant raw materials, as opposed to synthetic polymers, which are obtained by chemical synthesis.

Within the meaning of the invention, "beauty booster" means an agent that improves the attractiveness of the face perceived by a third party. Attractiveness is assessed on the basis of the overall improvement of the face by comparing photographs before and after treatment.

Within the meaning of the invention, "filmogenic" means a biopolymer having a filmogenic effect, i.e. a biopolymer soluble at the concentration of 7% by weight in water or at the maximum concentration at which it forms a homogeneous appearance and producing, once dried for 24 h at 40° C., a film that requires a mass of at least 100 g to break it in the test described in the present application.

"Filmogenic effect" means an effect that can create on the surface of the skin a film imperceptible to the naked eye, and thus protect the skin from external aggressions such as pollution and allergens.

"Tensor effect" means a tightening effect on the skin and by this tightening effect, smoothing the skin, reducing the skin's pores and causing the immediate reduction of wrinkles and fine lines.

Within the meaning of the invention, "tensor" means a biopolymer having a tensor effect, i.e. any biopolymer soluble at the concentration of 7% by weight in water or at the maximum concentration at which it forms a medium of homogenous appearance and producing at this concentration a retraction with a score of at least "+++" in the test described in the present application.

Within the meaning of the invention, "average molar mass" of a mixture of molecules means the average of weighted molar masses of each molecule of the mixture.

"Medium of homogenous appearance" means a medium having no aggregates visible to the naked eye.

Within the meaning of the invention, "cross-linked" means a biopolymer in which a three-dimensional network has been formed by means of the formation of chemical or physical bonds between the molecules of the biopolymer.

DETAILED DESCRIPTION OF THE INVENTION

The invention relates to a cosmetic or dermocosmetic agent formed by:
galactomannans obtained from *Caesalpinia spinosa* with molar masses of between 1 and 150 kDA,
and cross-linked sulfated galactans obtained from *Kappaphycus alvarezii* with molar masses of between 1 and 150 kDa, preferably between 7 and 40 kDa.

This agent consists of particular, selected biopolymers, with specific characteristics.

The molar masses of these biopolymers of a saccharide nature are preferably determined by steric exclusion chromatography. This method of liquid chromatography makes it possible to separate the macromolecules according to their hydrodynamic volume (steric exclusion chromatography). The solutes are eluted in the order of decreasing molar masses after passing through 3 gel permeation columns mounted in series (PL aquagel-OH C60, C40 and C30 columns). The compounds are detected by a refractive index detector. The molar masses of the carbohydrates are assessed by comparing the peak retention times detected in the samples of agents according to the invention with the retention times of standards injected beforehand. The average molar mass of a mixture of molecules corresponds to the average of molar masses weighted by the intensity of each one. For example, the association of biopolymers, the chromatogram of which is shown in FIG. 1C, contains polysaccharides with molar masses of between 1.2 and 150 kDa, and has an average molar mass of 16 kDa.

From a physical point of view, the agent of the invention has a low viscosity. The viscosity is measured at room temperature with the aid of a Brookfield DV-I+ model viscometer. The Brookfield viscometer determines the viscosity of a fluid on the basis of the deformation exerted on a spring created by rotating a disc in this fluid. A product is considered to be viscous if its viscosity exceeds 1000 centipoises.

Furthermore, this agent has a tensor effect. This tensor effect can be defined by the characterization of the retraction force on the synthetic skin model or by a sensory study involving a panel of experts.

The retraction force of a biopolymer can be characterized by an in vitro test. This model is known to a person skilled in the art and has been described in patent application EP1944065. The test is performed on a homogenous solution of biopolymers diluted in water at a concentration of 7% by weight. The homogenous mixture is deposited on a film of synthetic skin of a thickness of around 100 μm and an initial width of 10 mm. After drying at 22±3° C. and 40±10% relative humidity, the synthetic skin has a retracted width due to the tension exerted by the deposited polymer.

This retraction is assessed visually and quantified on a scale of "−" to "++++" ("−": no tensor effect, "++++": maximum tensor effect), represented in FIGS. 2A to 2E.

With this test, a product is deemed to be tensor if the retraction scores at least "++".

The tensor effect can also be assessed by a sensory study involving a panel of experts. The study can be conducted by formulating the agents to be tested as a gel.

The perception of these effects is evaluated by sensory experts on the basis of an assessment score ranging from 1 to 10.

Each expert scores on a scale of 0 to 10 (0: no perceived tensor effect, 10: significant tensor effect) the intensity of the sensation perceived after the application of a product (agent according to the invention or placebo) to the crow's-foot. A score is awarded 3 minutes, 5 minutes and 10 minutes after application of the product.

The average of the scores obtained at each time interval is calculated for each expert.

A product is deemed to be tensor, if the average of the scores obtained exceeds 3.

Lastly, the agent according to the invention has a filmogenic effect. This filmogenic effect can be characterized by means of a texturometer. The principle is to quantify the weight to be applied in order to rupture the film on the test samples.

The samples are prepared as follows:
Drying solutions containing 7% biopolymers (w/w) for 24 h at 40° C.
Obtaining films of a thickness of between 30 and 40 µm.
The test sample is deposited on the surface of flexible and deformable foam, which allows a significant deformation to be imposed on the biopolymer film. The substrate consists of a 5 mm-thick elastomeric urethane foam that mimics the surface and elasticity of the skin.

The study can be performed using a TA-XTplus Texturometer, manufactured by the Stable Micro System Company.

A cylindrical punch exerts a mechanical stress on the sample at a constant displacement speed.

A curve of the weight exerted (g) as a function of time (sec) is obtained, from which it is possible to determine the mass required to achieve the rupture.

The mass required to break the samples depends on the viscoelastic properties of each sample. A product is deemed to be filmogenic if the mass exerted to break the film exceeds 100 g.

The cosmetic or dermocosmetic agent according to the invention contains the association of selected galactomannans of *Caesalpinia spinosa* and selected cross-linked sulfated galactans of *Kappaphycus alvarezii*.

The agent according to the invention is made up of galactomannans preferably selected according to their average molar mass of between 5 and 30 kDa, i.e. preferably obtained by transformation of native galactomannans of *Caesalpinia spinosa*, preferably by hydrolysis.

These selected galactomannans more preferably have an average molar mass of between 8 and 25 kDa.

The selected specific galactomannans according to the invention are created as follows:
Solubilization of powder of native galactomannans of *Caesalpinia spinosa* in water at the proportion of at least 20 g/l,
Hydrolysis performed chemically or enzymatically; the size of the biopolymers is inversely proportional to the duration of hydrolysis or to the concentration of enzymes or chemical agent used,
Separation of the soluble and insoluble phases, in order to eliminate the insoluble phase,
Selection by membrane filtration(s) of galactomannans with an average molar mass of between 5 kDa and 30 kDa.

A low-viscosity liquid product A is obtained, containing selected galactomannans and with an average molar mass of between 5 and 30 kDa, preferably between 8 kDa and 25 kDa.

The size of the selected galactomannans is determined by steric exclusion chromatography.

The tensor effect is assessed on a retraction model on synthetic skin or by the panel of sensory experts.

The viscosity is determined by a viscometer.

The mass causing the rupture of the film made with the agent is assessed by a texturometer.

The characteristic results of several examples of galactomannans obtained from *Caesalpinia spinosa*, with an average molar mass of between 5 and 30 kDa, on the one hand, and galactomannans, with an average molar mass beyond that of the subject-matter of the invention, on the other, are given in Table 1 below:

TABLE 1

| Min & Max Molar Masses | Average Molar Mass | Viscosity (CP) or physical state | Tensor Effect on Retraction Model | Sensory Tensor Effect | Mass causing Rupture of Film (g) |
|---|---|---|---|---|---|
| | 4.7 kDa | Liquid | − | | |
| 0.5 to 40 kDa | 5.4 kDa | 70 | + | NT** | NT** |
| | 7.2 kDa | Liquid | + | | |
| 0.7 to 62 kDa | 9.5 kDa | Liquid | ++ | | |
| | 10 kDa | 85 | +++ | NT** | NT** |
| 0.9 to 117 kDa | 13.5 kDa | Liquid | +++ | | |
| | 18 kDa | 90 | +++ | 4.5 | 280 |
| 1.2 to 171 kDa | 19 kDa | Liquid | +++ | | |
| 1.5 to 215 kDa | 22 kDa | Liquid | +++ | | |
| 1.6 to 160 kDa | 25 kDa | Liquid | +++ | | |
| | 28.8 kDa | Slightly Viscous | + | NT** | NT** |
| | 38 kDa | Viscous | − | | |
| Non-hydrolyzed Tara Gum | 1980 kDa | >3125 | − | NT** | NT** |

NM*: Not Measured;
NT**: Not Tested

These results clearly show that native galactomannans with a high average molar mass (>30 kDa) and galactomannans with a low average molar mass (<5 kDA) do not have the desired tensor effect on the retraction model.

The tensor effect shown on the retraction model on synthetic skin is correlated by assessment of the tensor effect perceived by a panel of sensory experts. This confirms that the selected galactomannans according to the invention can be detected as having a tensor effect on the retraction model, either by a panel of sensory experts or by the desired filmogenic effect measured on the texturometer.

Galactomannans with an average molar mass of between 5 and 30 kDa, preferably between 8 and 25 kDa, do indeed have a tensor and filmogenic effect.

In addition to these galactomannans, the cosmetic or dermocosmetic agent according to the invention contains cross-linked sulfated galactans selected according to their average molar mass of between 5 and 25 kDa. They are obtained by the transformation of native sulfated galactans of *Kappaphycus alvarezii*, preferably by hydrolysis. In the invention, the particular selected sulfated galactans are created as follows:
Solubilization of powder of native galactomannans of *Kappaphycus alvarezii* in water at the proportion of at least 20 g/l,
Hydrolysis performed chemically or enzymatically; the size of the biopolymers is inversely proportional to the duration of hydrolysis or to the concentration of enzyme or chemical agent used,
Separation of the soluble and insoluble phases, in order to eliminate the insoluble phase,
Selection of the sulfated galactans with an average molar mass of between 5 kDa and 25 kDa by membrane filtration(s).

A low-viscosity liquid product B1 is obtained, containing selected sulfated galactans and with an average molar mass of between 5 and 25 kDa.

These sulfated galactans, selected according to their molar masses, are cross-linked by a cross-linking agent, preferably a cross-linking agent of an ionic nature. The ionic cross-linking agent is chosen from mono- or multi-valent cations. Other ionic cross-linking agents known to a person skilled in the art can be envisaged.

A low-viscosity liquid product B2 is obtained, containing selected cross-linked sulfated galactans having an average molar mass of between 5 and 25 kDa.

The characterization of the size of the sulfated galactans is achieved by steric exclusion chromatography.

The tensor effect is assessed on a retraction model on synthetic skin or by the panel of sensory experts.

The viscosity is determined by a viscometer.

The characteristic results of several examples of sulfated galactans obtained from *Kappaphycus alvarezii* with an average molar mass of between 5 and 25 kDa, on the one hand, and with an average molar mass beyond that of the subject-matter of the invention, on the other, are given in Table 2a.

Figure 1B:
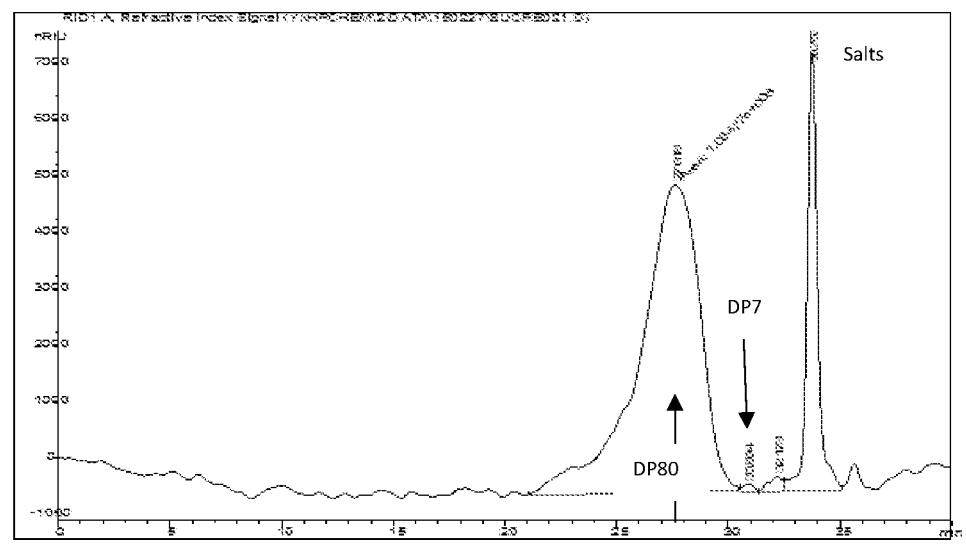
FIG. 1B represents the chromatogram of a component B1.
Figure 1C:
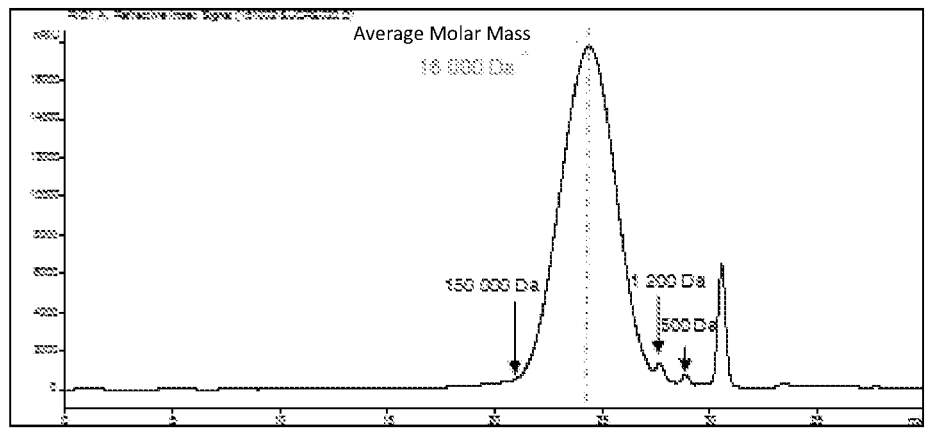
FIG. 1C represents the chromatogram of an agent according to the invention.
Figure 2A:
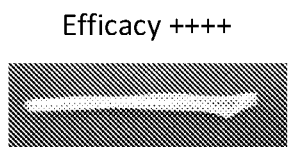
FIGS. 2A to 2E represent the scale of "−" (FIG. 2E) to "++++" (FIG. 2A) enabling the retraction force of a polymer to be assessed.
Figure 2B:
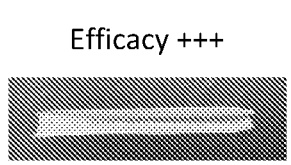
Figure 2C:
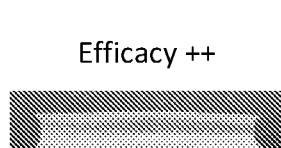
Figure 2D:
Figure 2E:

The chromatographic profiles of two tests are shown in FIGS. 1A and 1B. The characteristic results of several examples of cross-linked sulfated galactans are given in Table 2b.

TABLE 2a

| Min/Max Molar Masses | Average Molar Mass | Viscosity (CP) or Physical State | Tensor Effect on Retraction Model | Tensor Effect on Sensory Panel |
|---|---|---|---|---|
| 0.18 to 8.1 kDa (FIG. 1A) Product FR2986430 | <3.24 kDa | liquid | – | |
| | 3.6 kDa | 2.2 | – | NT** |
| 0.9 to 36.3 kDa | 5.4 kDa | 15 | + | NT** |
| 1.3 to 66.1 kDa | 10.8 kDa | 300 | +++ | 3.6 |
| 1.8 kDa to 150 kDa (FIG. 1B) | 14.4 kDa | liquid | +++ | |
| 2.2 to 97.5 kDa | 18 kDa | liquid | ++ | NT** |
| | 25 kDa | with Low Viscosity | ++ | |
| | 30 kDa | Viscous | + | |
| | 40 kDa | Viscous | + | |
| Non-hydrolyzed Kappa carrageenans | 1500 kDa | >3125 | – | NT** |

NM*: not measured,
NT**: not tested

The chromatographic profile in FIG. 1a shows that carbohydrates have molar masses of between 0.18 kDA (DP1) and 8.1 kDa (DP48), and that the average molar weight of this test is well below 3.24 kDa (DP18).

The chromatographic profile of FIG. 1b shows that carbohydrates have molar masses of between 1.8 kDa (DP7) and 150 kDa (DP833), and that the average molar mass of this test is in fact 14.4 kDa (DP80).

The results described in Table 2a show that sulfated galactans with a high average molar mass (≤30 kDa) and sulfated galactans with a low average molar mass (<5 kDa) do not have the desired physical state or tensor effect.

Sulfated galactans with an average molar mass of between 5 and 25 kDa, preferably between 8 and 20 kDa indeed have the desired physical state and a tensor effect shown either by a retraction force, or validated by the sensory experts.

TABLE 2b

| Average Molar Mass | cross-linking | Viscosity (CP) | Tensor Effect on Retraction Model | Tensor Effect on Sensory Panel |
|---|---|---|---|---|
| Product FR2986430 <3.24 kDa | No | Liquid | – | NT** |
| | Yes - agent 1 | Liquid | – | NT** |
| | Yes - agent 2 | Liquid | – | NT** |
| | Yes - agent 3 | Liquid | – | NT** |
| 3.6 kDa | No | 2.2 | – | NT** |
| | Yes - agent 1 | Liquid | – | NT** |
| | Yes - agent 2 | Liquid | – | NT** |
| | Yes - agent 3 | Liquid | – | NT** |
| 10.8 kDa | No | 300 | +++ | 3.6 |
| | Yes - agent 1 | Liquid | +++ | NT** |
| | Yes - agent 2 | Liquid | +++ | NT** |
| | Yes - agent 3 | Liquid | ++++ | 4.5 |
| | Yes - agent 4 | Liquid | ++++ | NT** |
| 18 kDa | No | Liquid | ++ | NT** |
| | Yes - agent 3 | Liquid | +++ | NT** |

NT**: Not Tested
Agent 1 and 2 are bivalent-cation type ionic cross-linking agents
Agent 3 is a monovalent-cation type ionic cross-linking agent
Agent 4 is a multivalent-cation type ionic cross-linking agent The cosmetic or dermocosmetic agent according to the invention is formed both by particular galactomannans and particular cross-linked sulfated galactans, as described above.

The method for creating the agent according to the invention comprises the following steps:
  obtaining galactomannans with an average molar mass of between 5 and 30 kDa, the above-mentioned Product A according to the protocol previously described,
  obtaining cross-linked sulfated galactans with an average molar mass of between 5 and 25 kDa, the above-mentioned Product B2 according to the protocol previously described,
  mixing Product A and Product B2.

A filtration step can be added after mixing.

According to a particularly appropriate embodiment, the cosmetic or dermocosmetic agent according to the invention is formed:
  between 60 and 90% by galactomannans and
  between 10 and 40% by cross-linked sulfated galactans.

Even more preferably, the cosmetic or dermocosmetic agent according to the invention is formed:
  between 70 and 90% by galactomannans and
  between 10 and 30% by cross-linked sulfated galactans.

Preferably, the galactomannans and cross-linked sulfated galactans together form an interpenetrated network.

Several agents, in the form of solutions, were tested at 7% on the model of synthetic skin and at 0.5% in the sensory tensor study.

The results are given in the tables below:
  in Table 3a, the combinations with 80% galactomannans and 20% cross-linked sulfated galactans
  in Table 3b, the combinations with galactomannans and cross-linked sulfated galactans with an average molar mass selected according to the invention.

TABLE 3a

| Min/Max Molar Mass | 20% Cross-linked Sulfated Galactans of Kappaphycus alvarezii | 80% Galactomannans of Caesalpinia spinosa | Physical State | Tensor Effect on Retraction Model | Tensor Effect on Sensory Panel | Filmogenic Effect measured by texturometer (g) |
|---|---|---|---|---|---|---|
| | <3.24 kDa | 4.7 kDa | Liquid | − | | |
| | <3.24 kDa | 19 kDa | Liquid | ++ | | |
| 0.7 to 70 kDa | 7.2 kDa | 10 kDa | Liquid | ++ | | |
| | 7.2 kDa | 16 kDa | Liquid | ++++ | | |
| | 7.9 kDa | 11.7 kDa | Liquid | ++++ | | |
| 0.9 to 117 kDa | 9.4 kDa | 13.3 kDa | Liquid | ++++ | | |
| | 12.8 kDa | 20.7 kDa | Liquid | ++++ | | |
| 1.2 to 171 kDa | 14.4 kDa | 19 kDa | Liquid | ++++ | 5.1 | 371 |
| 0.9 to 117 kDa | 14.8 kDa | 13.5 kDa | Liquid | ++++ | | |
| 1.5 to 190 kDa | 16.4 kDa | 20.2 kDa | Liquid with Low Viscosity | ++++ | | |

NT**: Not Tested

These results show that selecting cross-linked sulfated galactans according to their average molar mass (5 to 25 kDa, preferably 8 to 20 kDa) and selecting galactomannans according to their average molar mass (5 to 30 kDa, preferably 8 to 25 kDa) is necessary in order to obtain the expected result.

The galactomannan/cross-linked sulfated galactan combination in which either the cross-linked sulfated galactans or the galactomannans or both have average molar masses beyond the selection of the invention, do not allow the physical state and the expected tensor and filmogenic effect to be obtained. It will be observed that the association of cross-linked selected sulfated galactans and galactomannans selected according to the invention makes it possible not only to preserve the tensor effect of retraction of the cross-linked selected sulfated galactans or selected galactomannans, but above all to reinforce the tensor efficacy perceived by the panel of sensory experts.

TABLE 3b

| Selected Sulfated Galactans (SSG) of Kappaphycus alvarezii (8-20 kDa) | Selected Galactomannans (SGm) of Caesalpinia spinosa (8-25 kDa) | Tensor Effect on retraction model | Tensor Effect on sensory panel | Filmogenic Effect measured by texturometer (g) |
|---|---|---|---|---|
| 10% cross-linked SSG | 90% SGm | +++ | 4.4 | NT** |
| 20% cross-linked SSG | 80% SGm | ++++ | 5.1 | 371 |
| 30% cross-linked SSG | 70% SGm | +++ | 3.8 | NT** |
| 50% cross-linked SSG | 50% SGm | ++ | NT** | NT** |
| 20% cross-linked SSG | — | +++ | 4.1 | NT** |
| | 80% SGm | +++ | 4.3 | NT** |

NT**: Not Tested

These results show the surprising effect of the interaction of the two polysaccharides of selected sizes. For example, for the 20%/80% combination, the tensor effect of the retraction model is potentiated in the combination. A similar effect is observed by the sensory panel assessing the tensor effect.

Thus, the combinations containing between 10 and 40% cross-linked sulfated galactans with between 90% and 60% galactomannans have the expected efficacy, a tensor and filmogenic effect.

By contrast, it will be observed that the 50%/50% combination of two compounds of selected sizes does not have such a potentiated tensor effect on the retraction model as the other combinations according to the invention.

This association also makes it possible to increase the resistance of the film compared to the resistance of the films of selected galactomannans or selected sulfated galactans only.

The association of cross-linked selected sulfated galactans and selected galactomannans in fact forms an interpenetrated network.

The presence of this network is shown by the revelation of the presence of a homogenous mixture by measuring on an AFM (Atomic Force Microscope) and the change in mobility of the polymer chains forming the network by DSC (Differential Scanning calorimetry) and DMA (Dynamic Mechanical Analysis) studies.

The principle of operation of the AFM involves probing the surface of a sample by subsequent scanning by a very fine probe located in the immediate vicinity of this surface. The AFM probe consists of a flexible lever with a tip fixed at its end.

The sample is fixed on a piezoelectric ceramic. This ceramic allows movements in the three directions in space.

The atomic force microscope makes it possible to see both complex biological structures and individual molecules in their functional state. The lateral and vertical resolutions can reach several angstroms. Depending on the method of measurement (contact, tapping, no contact) and the functionalization of the probe, the atomic force microscope makes it possible to measure intra- and inter-molecular forces and affinities between molecules and perform microrheology or even assess the topology of a surface.

The samples analyzed by AFM were pre-prepared by spin coating.

Figure 3:
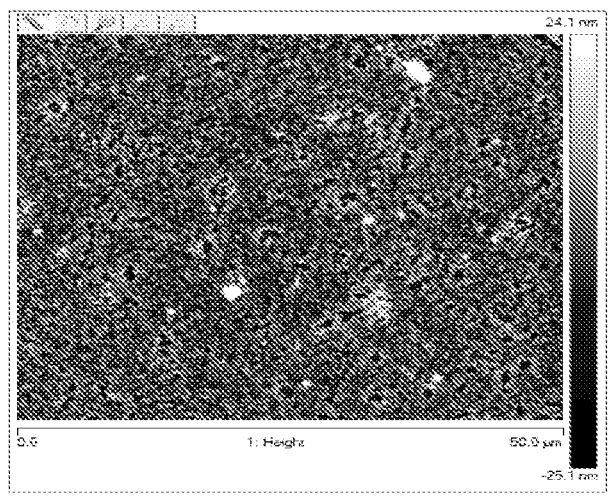
FIG. 3 represents the AFM (Atomic Force Microscope) image of an agent according to the invention.

The topology obtained by AFM of the film of the agent according to the invention (cross-linked sulfated galactans and galactomannans—ex2) is shown to a scale of 50 μm (FIG. 3).

The AFM image of the association of cross-linked sulfated galactans and galactomannans according to the invention shows that the mixture is homogenous and that there are no micro-domains of each polymer. The surface roughness of the agent according to the invention is 7 nm.

The changes in state of the polymers involve processes that are endothermic (fusion, for example) or exothermic (crystallization, for example). These thermal exchanges can be measured by differential enthalpic analysis (DSC). If the degree of interpenetration of two polymers is not high, the two networks will be divided into two phases and, in this case, two glass transition temperatures corresponding to each of the networks taken individually will be detected. In the case of an interpenetrated network, only one glass transition temperature will be detected at an intermediate temperature between those of the two networks combined.

Figure 4A:
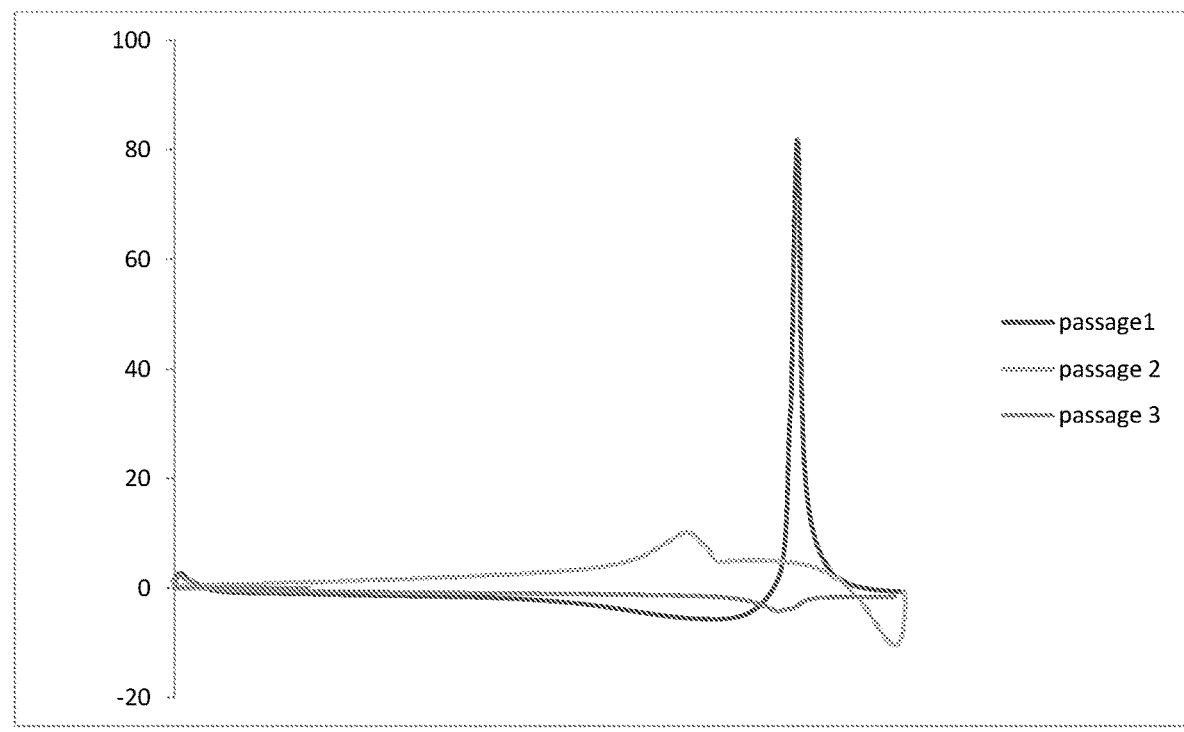
FIGS. 4A to 4F represent the DSC (Differential Scanning calorimetry) curves for selected sulfated galactans according to the invention (FIG. 4A and FIG. 4B), for selected galactans according to the invention (FIG. 4C and FIG. 4D) and for an agent according to the invention (FIG. 4E and FIG. 4F)
Figure 4B:
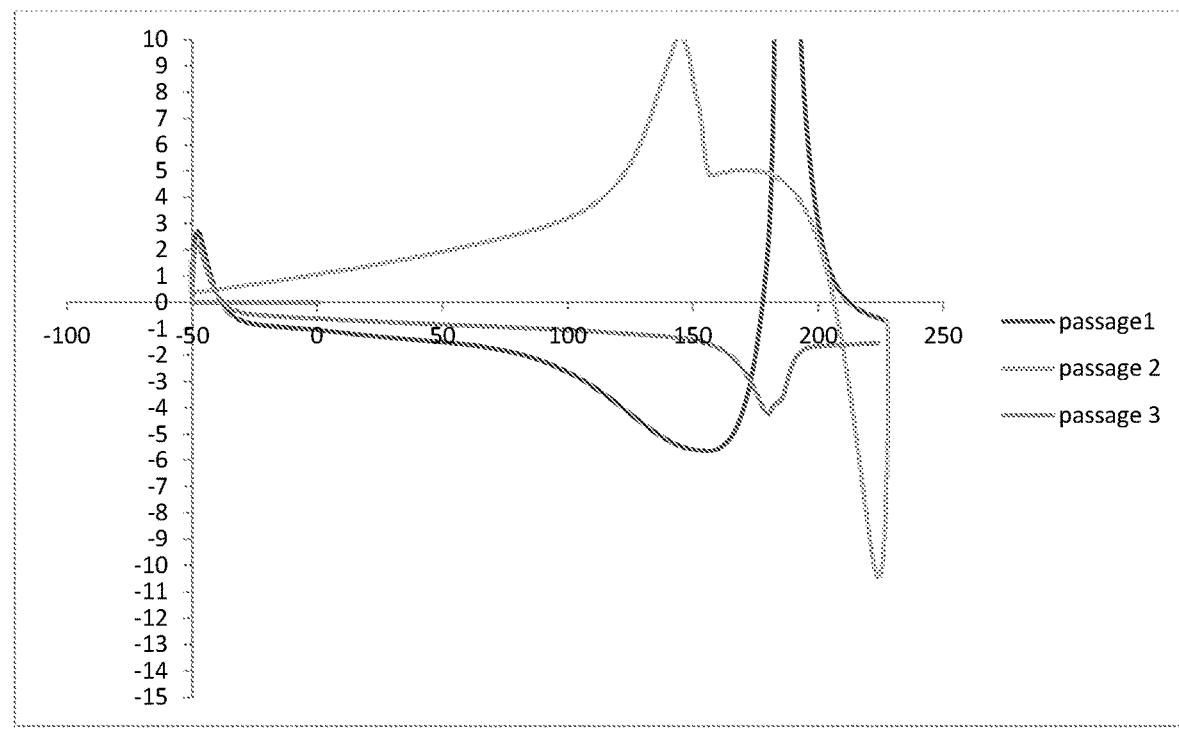
Figure 4C:
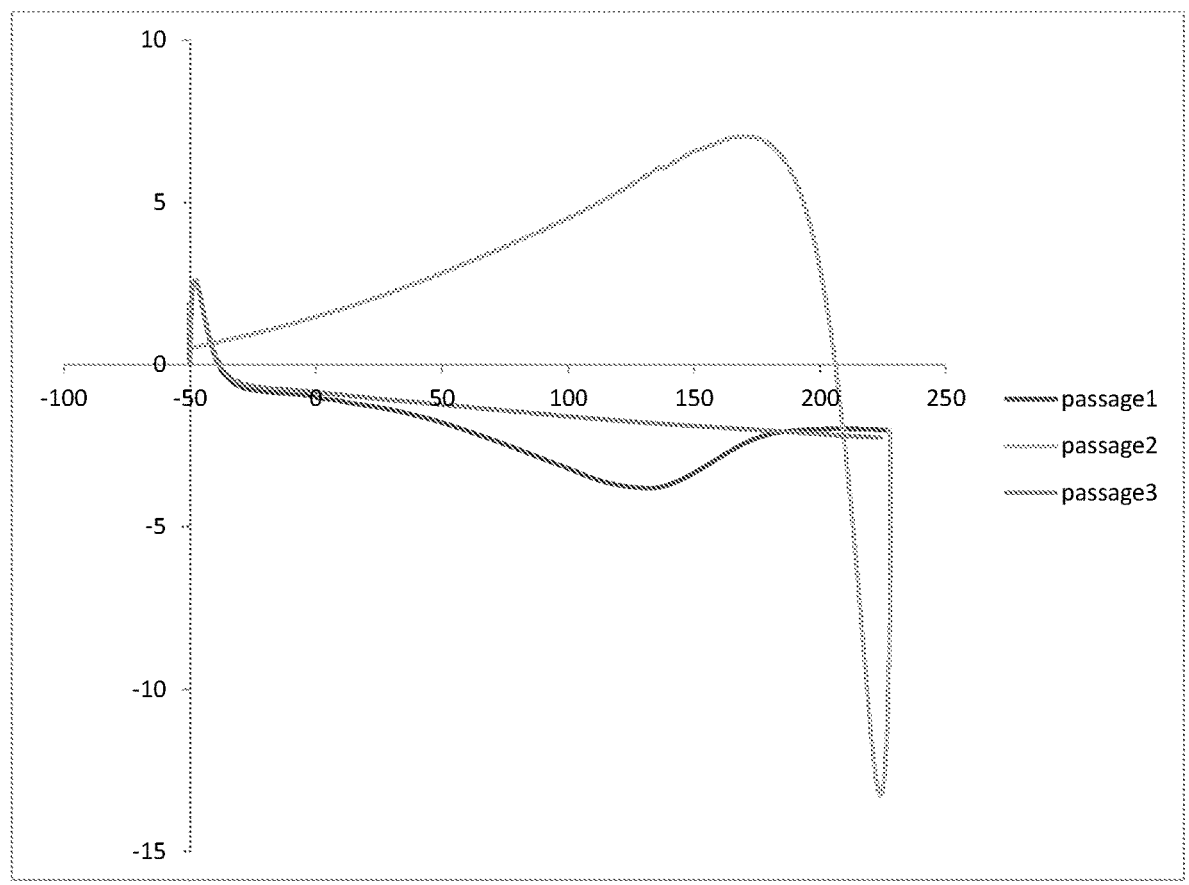
Figure 4D:
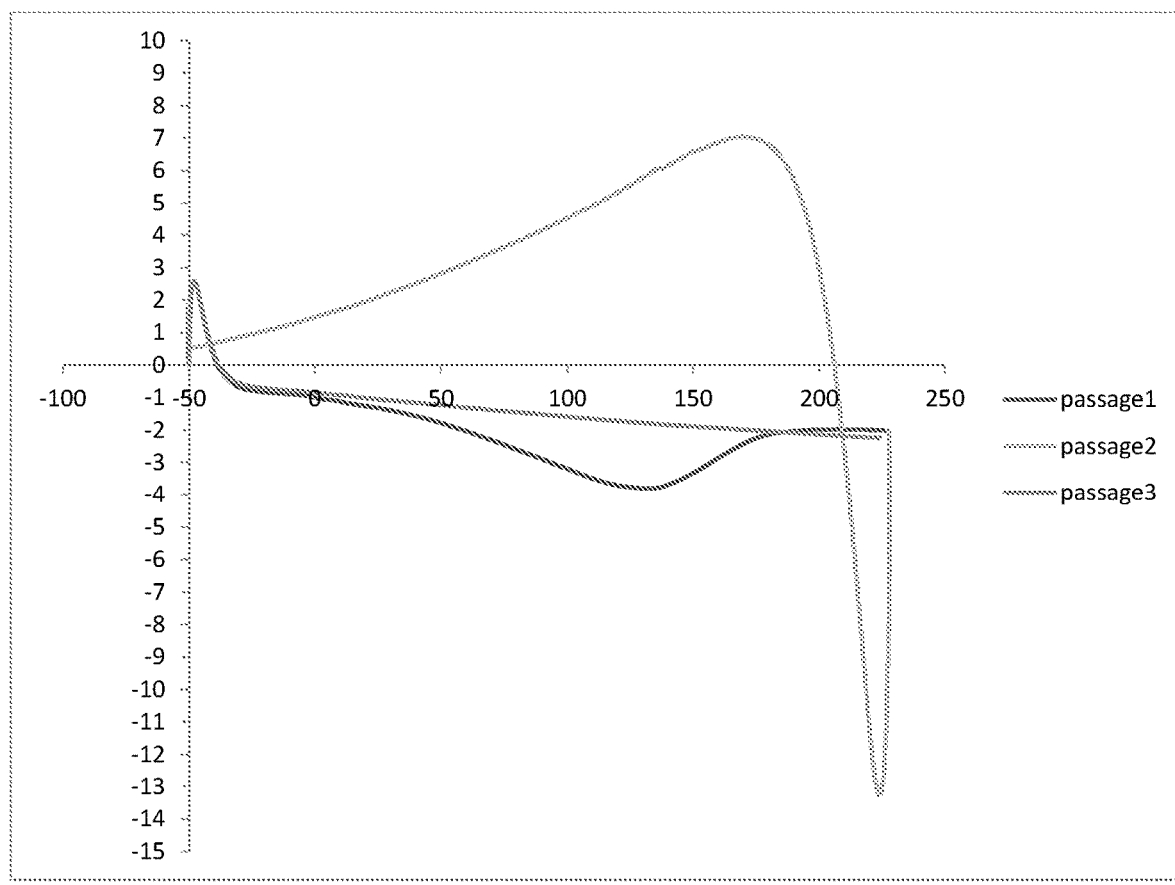
Figure 4E:
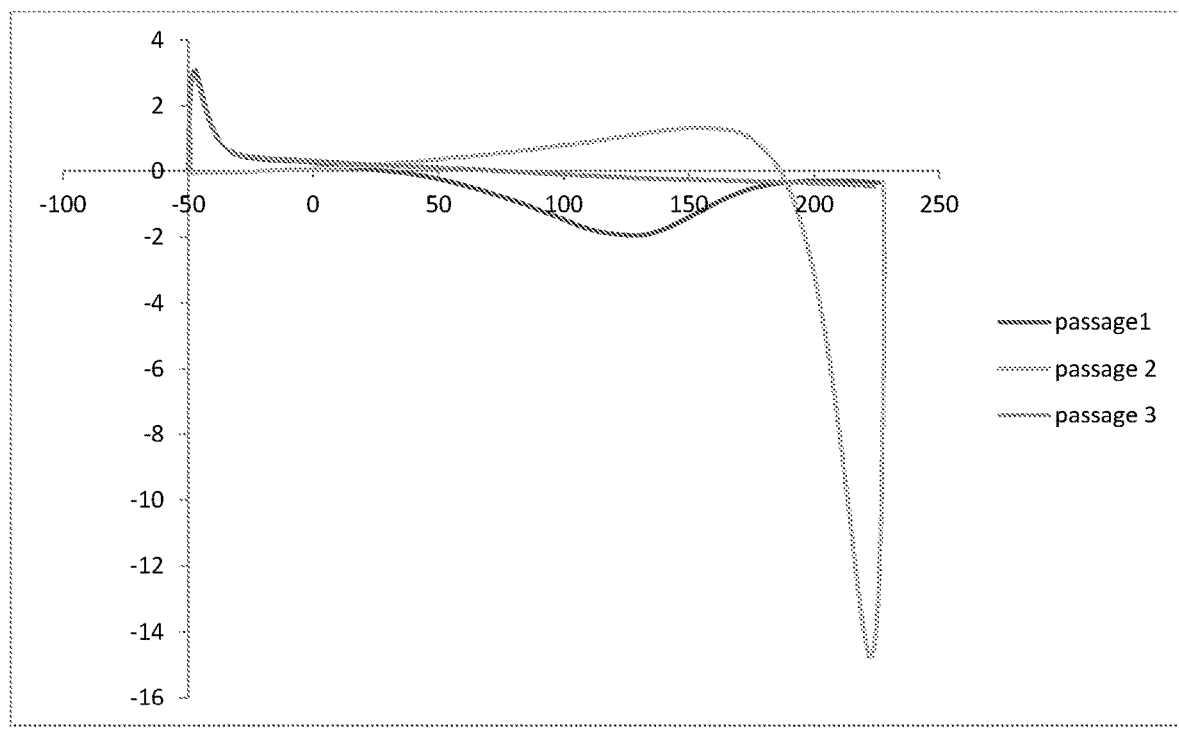
Figure 4F:
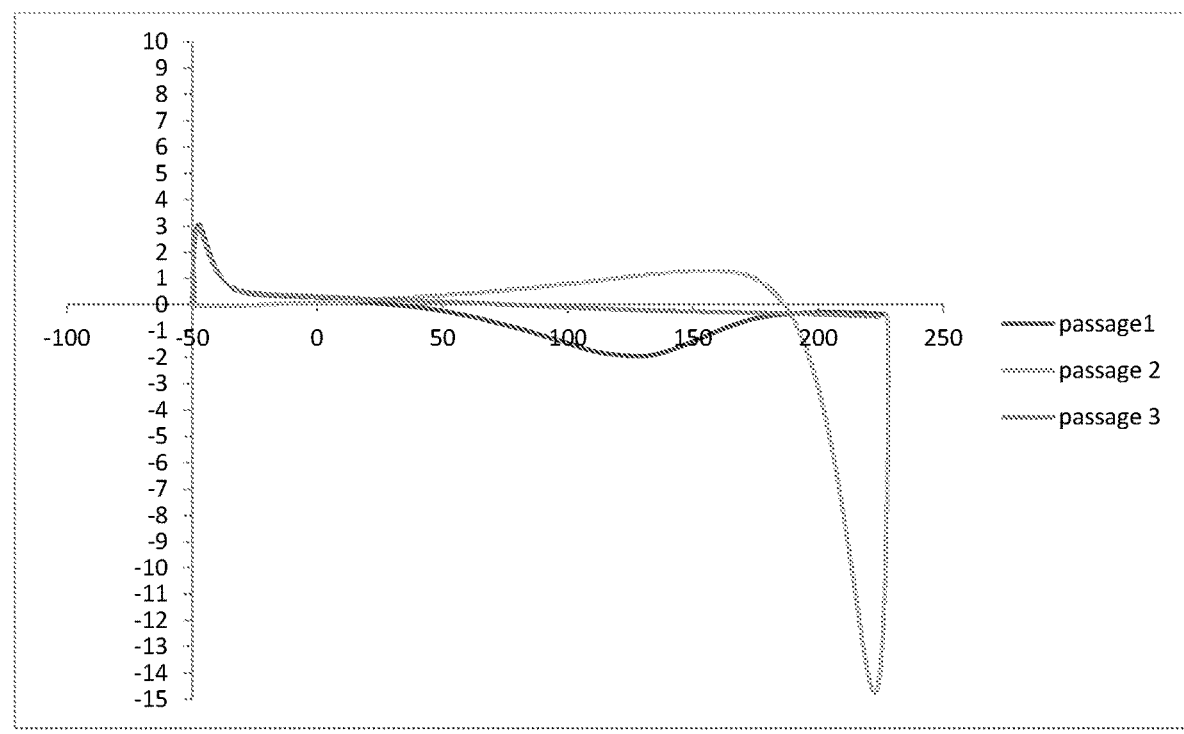

The samples tested were selected cross-linked sulfated galactans with an average molar mass of 10.8 kDa (FIG. 4A and FIG. 4B), selected galactomannans with an average molar mass of 10 kDa (FIG. 4C and FIG. 4D) and the association of these cross-linked selected sulfated galactans and these selected galactomannans (FIG. 4E and FIG. 4F).

The comparison of the spectra of the single biopolymers and the association (examples of Example 1) show a change in the thermal behavior of the association compared to the single biopolymers. In fact, despite the sulfated galactans/galactomannans distribution, it will be observed that there is no exothermic peak for the association but there is one in the sample of cross-linked sulfated galactans. Moreover, the characteristic endotherm of a fusion of crystalline areas of cross-linked sulfated galactans is absent in the association suggesting a homogenous distribution of the two cross-linked sulfated galactan and galactomannan networks, limiting the establishment of a crystalline zone attributable to the cross-linked sulfated galactans.

Dynamic mechanical thermal analysis (DMA) is commonly used to show the presence of different phases in the mixtures of polymers. If there is no combination of two polymers, two mechanical relaxation temperatures will be observed, one for each polymer. If the combination of two polymers is perfectly homogenous, only one mechanical relaxation temperature is observed. It is generally situated between the mechanical relaxation temperature of the two polymers making up the combination.

Mechanical relaxation is assessed by means of a parameter called Tan delta. If the interactions are sufficiently strong in the mixture of two polymers, an additional Tan delta peak can be observed.

Figure 5A:
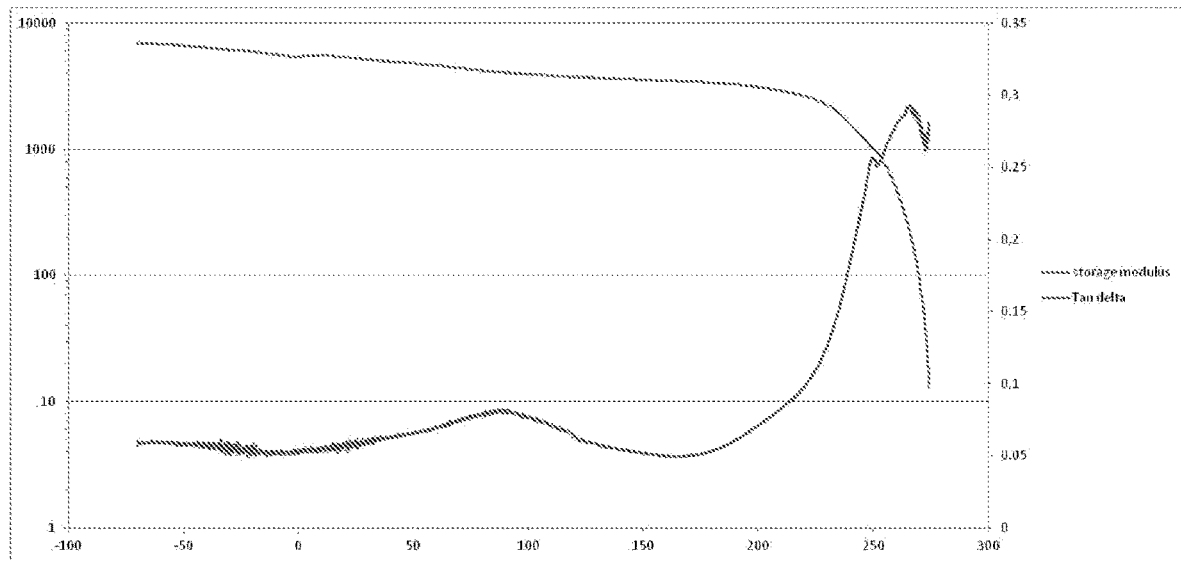
FIGS. 5A to 5D represent the DMA (Dynamic Mechanical Analysis) curves for the selected galactomannans according to the invention (FIGS. 5A-5B) and for an agent according to the invention (FIGS. 5C-5D)
Figure 5B:
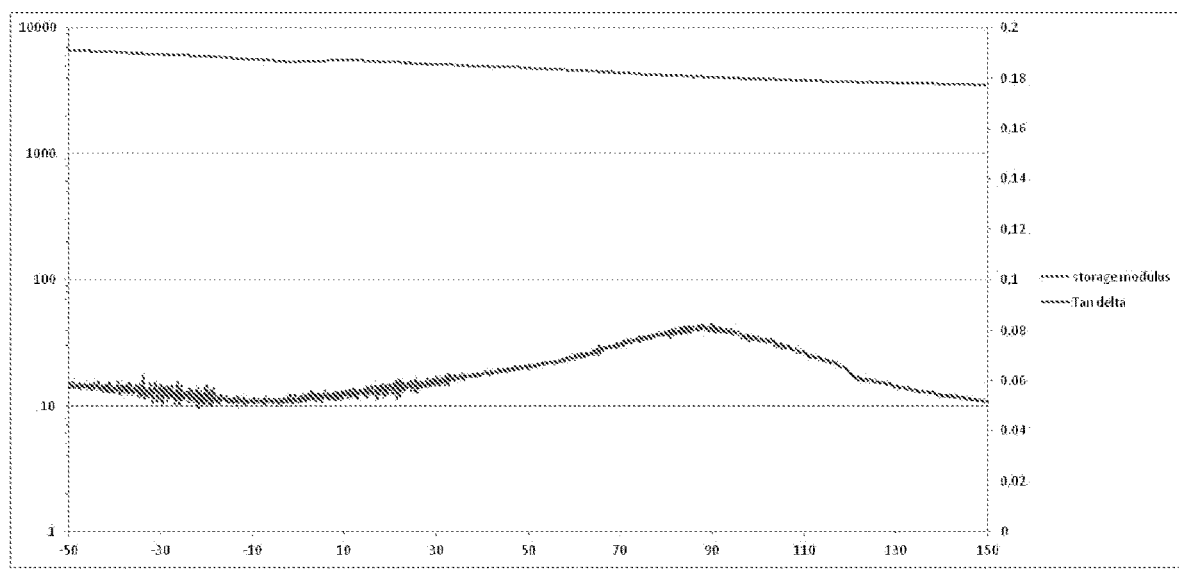

On the selected galactomannans DMA curve (−70 to 300° C., FIG. 5A, and −50 to 150° C. magnification, FIG. 5B) the presence of a Tan delta peak at 90° C. can be seen.

Figure 5C:
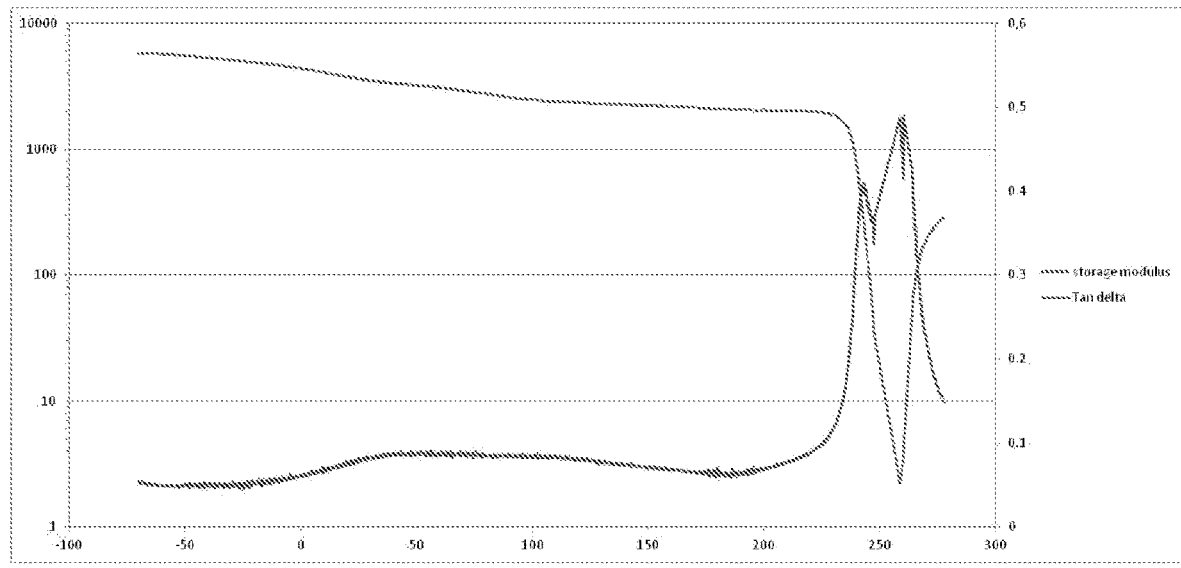
Figure 5D:
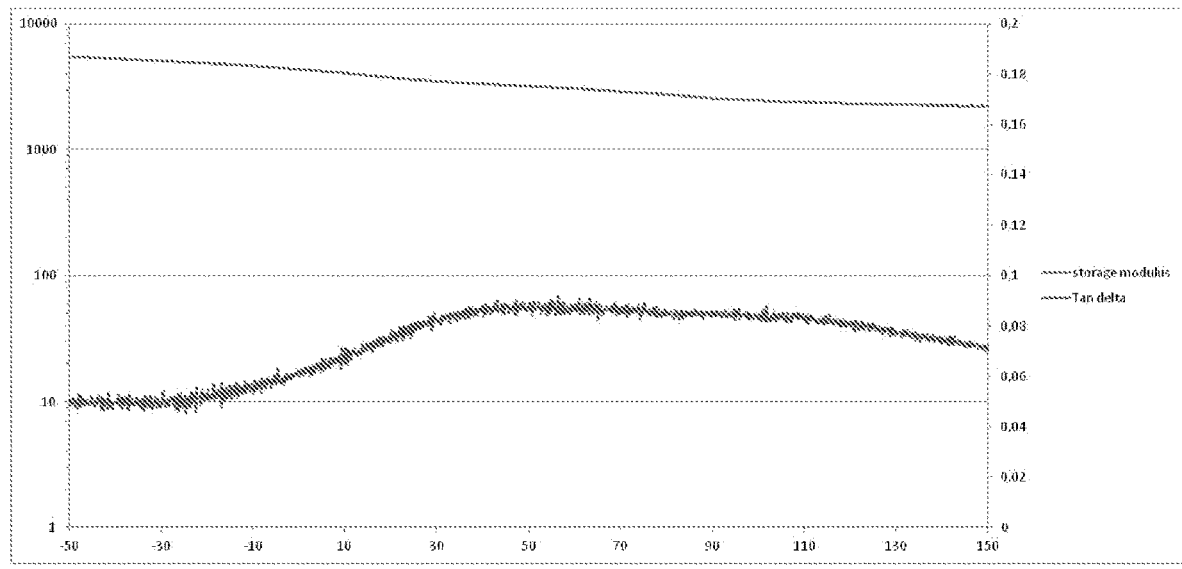

The DMA curve of the agent according to the invention, associating the galactomannans and cross-linked sulfated galactans (−70 to 300° C., FIG. 5C, and −50 to 150° C. magnification, FIG. 5D), has a very wide profile towards 40 and 100° C. showing a more extended mechanical relaxation temperature than those of galactomannans only.

This change in the Tan delta can only take place because the two networks have no phase separation and are sufficiently close to one another. As this widening of the Tan delta is not accompanied by the presence of two distinct peaks, it suggests the presence of two networks interacting with one another.

The changes in relaxation (DMA) and glass transition (DSC) temperatures of the agent according to the invention show that there is a homogenous distribution of the two biopolymer networks. They also suggest that there is interaction between these two biopolymers relating to an interpenetrated biopolymer network.

The cosmetic or dermocosmetic agent according to the invention can therefore be used for its different properties. In particular, the invention relates to its use as a tensor and/or filmogenic cosmetic or dermocosmetic agent.

It can thus be used in particular as an agent:
for a cosmetic or dermocosmetic effect to protect the skin against the penetration of toxic molecules, such as pollutants, allergens, irritants or heavy metals and/or the bacterial adhesion of *Staphylococcus aureus*, and/or to improve the barrier effect of the skin, and/or
for a lifting-film cosmetic or dermocosmetic effect in order to improve the radiance of the skin and/or smooth the skin, and/or
for a perceptible film cosmetic effect, in order to feel the tensor efficacy, improve the overall appearance of the face and encourage the hold of make-up pigments and/or
for a second skin film and beauty booster effect.

Due to these different efficacies, the invention also relates to its use to combat the telltale signs of skin ageing.

The subject-matter of the invention therefore also concerns:
the non-therapeutic cosmetic use of an agent according to the invention:
as a tensor and/or filmogenic cosmetic agent, and/or
as a cosmetic agent to improve the barrier effect of the skin, and/or
to improve the radiance of the skin and/or smooth the microrelief of the skin and/or smooth wrinkles, and/or
to combat the telltale signs of ageing of the skin, and/or
to encourage make-up hold and/or improve the dispersion of pigments in cosmetic formulations, and/or
to give a second skin, beauty booster effect.
the cosmetic agent according to the invention for use:
in the protection of the skin,
in the protection of the skin against the penetration of toxic molecules,
in the protection of the skin against the bacterial adhesion of pathogens.

The cosmetic and/or dermocosmetic agent according to the invention is preferably used in a composition, this composition comprising a cosmetically acceptable medium. These compositions are in different dosage forms, suitable for topical administration onto human skin.

These compositions can specifically be in the form of oil-in-water emulsions, water-in-oil emulsions, multiple emulsions (Water/Oil/Water or Oil/Water/Oil) that may be microemulsions or nanoemulsions, or in the form of solutions, suspensions, hydrodispersions, aqueous gels or powders. They can be more or less fluid and have the appearance of a cream, a lotion, a milk, a serum, an ointment, a gel, a paste or a foam, or be in solid form.

They may be compositions comprising at least 0.01% of an agent according to the invention, preferably between 0.05 and 0.5%.

These compositions comprise, in addition to the active ingredient, a physiologically acceptable and preferably cosmetically acceptable medium, i.e. that does not cause unacceptable sensations of discomfort for the user such as redness, stretching or tingling.

The compositions according to the invention can contain as an adjuvant at least one compound chosen from:
oils, that can be chosen specifically from silicone oils, linear or cyclic, volatile or non-volatile;
waxes, such as ozokerite, polyethylene wax, bees wax of carnauba wax,
silicone elastomers,
surfactants, preferably emulsifiers, whether non-ionic, anionic, cationic or amphoteric,
co-surfactants, such as linear fatty alcohols,
thickeners and/or gellants, humectants, such as polyols like glycerin,
organic filters,
inorganic filters,
dyes, preservatives, loads, pigments, minerals,
tensors,
sequestrants,
perfumes,
and their mixtures, without this list being limiting.

Examples of such adjuvants are cited particularly in the International Cosmetic Ingredient Dictionary and Handbook (CTFA), published by the Personal Care Product Council.

Clearly, a person skilled in the art will take care to choose any complementary compounds, active or non-active, and their quantity, so that the advantageous properties of the mixture are not, or not substantially, altered by the envisaged addition.

These compositions are particularly intended to be used for the effects produced by the cosmetic or dermocosmetic agent according to the invention. The invention also relates specifically to a cosmetic method of skin care to improve the condition of the skin, particularly to improve the skin's radiance and/or combat the telltale signs of skin ageing. Preferably, the method consists in applying at least once a day to the facial skin a composition comprising at least 0.05% by weight of dry matter of the cosmetic or dermocosmetic agent according to the invention.

In order to illustrate the invention, examples of the test results are given below.

EXAMPLES

Example 1: Examples of Agents According to the Invention

Several agents (shown in Table 4) according to the invention have been tested in the tests below. The results given for the tests to assess the effect of the agent according to the invention represent the average of the individual results of some of these agents.

TABLE 4

| Test | B Products Cross-linked Sulfated Galactans of *Kappaphycus alvarezii* | | A Products Galactomannans of *Caesalpinia spinosa* | | Tensor Effect on the Retraction Model |
|---|---|---|---|---|---|
| | Content | Average Molar Mass | Content | Average Molar Mass | |
| 1 | 20% | 7.2 kDa | 80% | 16 kDa | ++++ |
| 2 | 20% | 7.9 kDa | 80% | 11.7 kDa | ++++ |
| 3 | 20% | 9.4 kDa | 80% | 13.3 kDa | ++++ |
| 4 | 20% | 12.8 kDa | 80% | 20.7 kDa | ++++ |
| 5 | 20% | 14.4 kDa | 80% | 19 kDa | ++++ |
| 6 | 20% | 14.8 kDa | 80% | 13.5 kDa | ++++ |
| 7 | 20% | 16.4 kDa | 80% | 20.2 kDa | ++++ |
| 8 | 10% | 14.4 kDa | 90% | 19 kDa | +++ |
| 9 | 30% | 14.4 kDa | 70% | 19 kDa | +++ |

A person skilled in the art knows that the hydrolysis time and/or hydrolysis temperature must be changed in order to obtain sulfated galactan type biopolymers or galactomannans with the expected average molar masses. These agents are obtained according to a method comprising the following steps:

Preparation of Product A:
   Solubilization of power of native galactomannans of *Caesalpinia spinosa* in water at 20 g/l,
   Enzymatic hydrolysis performed for 20 mn to 6 h, at a temperature of between 20 and 60° C.,
   Filtration in order to separate the soluble and insoluble phases and eliminate the insoluble phase, Preparation of Product B:
   Solubilization of power of native sulfated galactans of *Kappaphycus alvarezii* in water at 20 g/l,
   Acid hydrolysis performed for 10 mn to 6 h, at a temperature of between 20 and 60° C.,
   Filtration in order to separate the soluble and insoluble phases and eliminate the insoluble phase, Mixing Product A and Product B,
Adding the cross-linking agent
Membrane filtration and selection of polysaccharides with molar masses of between 1 and 150 kDa.

Example 2: Example of an Emulsion-Type Composition According to the Invention

The emulsion was made using the following formula:

| | |
|---|---|
| Myristyl alcohol/Myristyl glucoside (Montanov 14-SEPPIC) | 5.00% |
| Isopropylpalmitate (DUB IPP-Stéarinerie DUBOIS) | 25.00% |
| Amyl cinnamaldehyde | 0.20% |
| AGENT ACCORDING TO THE INVENTION | 1.00% |
| Kathon CG (Rhom & Haas) | 0.05% |
| Water | 100% qs |

Example 3: Example of an Emulsified-Gel Type Composition According to the Invention The emulsified gel was made using the following formula:

| | |
|---|---|
| Cetearyl ethylhexanoate (Lanol 1688, Seppic) | 10.00% |
| Behenyl alcohol/Arachidyl glucoside/Arachidyl alcohol (Montanov 202, Seppic) | 3.00% |
| Polyacrylamide/C13-14 isoparaffin/Laureth-7 (Sepigel 305, Seppic) | 2.00% |
| Isonyl isononanoate (Lanol 99, Seppic) | 2.00% |
| Preservatives | 0.70% |
| Agent according to the invention | 0.05%, 0.10%, 0.25% or 0.50% |
| Water | 100% qs |

Example 4: Example of a Gel Type Composition According to the Invention

The gel was made using the following formula:

| | |
|---|---|
| Agent according to the invention | 0.05%, 0.10%, 0.25% or 0.50% |
| Preservative | 0.23% |
| Carbomer (Ultrez 10, Noveon) | 0.27% |
| Water | 100% qs |

Example 5: Example of a Serum Type Composition According to the Invention

The serum was made using the following formula:

| | |
|---|---|
| Glycerin | 3.0% |
| Propylene glycol | 2.0% |

| | |
|---|---|
| Dimethicone (DC200, Dow Corning) | 2.0% |
| Caprilic/capric triglyceride (DUB, MCT5545, Stearinerie Dubois) | 2.0% |
| PEG-7 glyceryl cocoate (DUB CG7, Stéarinerie Dubois) | 1.4% |
| Agent according to the invention | 1.0% |
| Preservatives | 1.0% |
| Cyclopentasiloxane/cyclohexasiloxane (Xiameter PMX-0345, Dow Corning) | 1.0% |
| Acrylates/C10-30 Alkyl acrylate crosspolymer (Carbopol Ultrez 20, Lubrizol) | 0.4% |
| Xanthan gum (Keltrol CG, Kelco) | 0.4% |
| Carrageenan (Satiagel ™ UTH 18, Cargill) | 0.2% |
| Water | 100% qs |

Example 6: Example of a Foundation Type Composition According to the Invention The foundation was made using the following formula:

| | |
|---|---|
| Cetyl PEG/PPG-10/1 Dimethicone (E1016, THOR) | 24.0% |
| PEG-12 Dimethicone (E1200, THOR) | 16.0% |
| Cyclopentasiloxane/Cyclohexasiloxane (XIAMETER PMX-0345, XIAMETER) | 10.0% |
| Methyl Trimethicone/Acrylate/Dimethicone Copolymer (KP-549, SHIN ETSU) | 8.0% |
| Titanium Dioxide (C.I. 77891) (SunPuro ™ TitaniumDioxyde, SUN CHEMICAL) | 7.4% |
| Heptyl glucoside (SEPICLEAR G7, SEPPIC) | 7.0% |
| Polydimethylsiloxyethyl Dimethicone (K-6028, SHIN ETSU) | 5.0% |
| Dimethicone/Trisiloxane/Ceteth-10/Laureth-4 (DC 7-3110, DOW CORNING) | 5.0% |
| Myristyl alcohol/Myristyl glucoside (MONTANOV 14, SEPPIC) | 4.0% |
| Octyldodecanol/Octydodecyl Xyloside/PEG-30 Dipolyhydroxystearate (EASYNOV, SEPPIC) | 3.0% |
| Methyl trimethicone (TMF 1.5, SHIN ETSU) | 2.0% |
| Zinc oxide (Zinc Oxide, DEGUSSA) | 2.0% |
| Titanium Dioxide/Butylene Glycol Dicaprylate/Dicaprate/ Silica/ Polyglyceryl-2 Dipolyhydroxystearate (EUSOLEX T OLEO, MERCK) | 2.0% |
| Iron Oxides (C.I. 77492) (SunPuro ™ Yellow Iron Oxide, SUN CHEMICAL) | 1.3% |
| Iron Oxides (C.I. 77499) (SunPuro ™ Black Iron Oxide, SUN CHEMICAL) | 1.2% |
| Cetearyl Alcohol/Cetearyl Glucoside (MONTANOV 68, SEPPIC) | 1.0% |
| Talc (HYTECH) | 1.0% |
| Preservatives | 0.7% |
| Oriza sativa (rice) starch (Rice Powder, HYTECH) | 0.7% |
| Agent according to the invention | 0.5% |
| Iron Oxides (C.I. 77491) (SunPuro ™ Red Iron Oxide, SUN CHEMICAL) | 0.4% |
| Candelilla cera (Candelilla Wax, HYTECH) | 0.3% |
| Mica, Iron oxide (CI 77019, CI 77491) (Mica, HYTECH) | 0.3% |
| Water | 100% qs |

Example 7: Example of a Cream Mask Type Composition

The cream mask was made using the following formula:

| | |
|---|---|
| Isonyl isononanoate (Lanol 99, Seppic) | 10.0% |
| Cetearyl ethylhexanoate (Lanol 1688, Seppic) | 5.0% |
| Behenyl alcohol/Arachidyl glucoside/Arachidyl alcohol (Montanov 202, Seppic) | 5.0% |
| Cetearyl alcohol/Cetearyl glucoside (Montanov 68, Seppic) | 50% |
| Propylene glycol | 3.5% |
| Preservatives | 0.7% |
| Agent according to the invention | 0.5% |
| Sodium alginate (Satialgine S550, Cargill) | 0.1% |
| Water | 100% qs |

Example 8: Example of a Cloth Mask Type Composition

The solution for soaking the cloth mask is as follows:

| | |
|---|---|
| MethylPropanediol (DUB DIOL, Stéarinerie Dubois) | 7.0% |
| Glycerol | 1.5% |
| Butylene glycol | 1.0% |
| Preservatives | 1.0% |
| Agent according to the invention | 0.5% |
| PEG-7 glyceryl cocoate (DUB CG7, Stéarinerie Dubois) | 0.2% |
| Carbomer (CARBOPOL U20, Lubrizol) | 0.2% |
| Sodium Dilaureth-7 Citrate (EUCAROL D, CESALPINIA) | 0.1% |
| Water | 100% qs |

Tests—Demonstration of the Efficacy of the Agent According to the Invention

The performance levels of the invention were assessed on the basis of 4 aspects:

It has a protective film effect, a lifting film effect, a perceptible film effect and a beauty-booster second skin film effect.

1) Protective Film Effect:

The agent according to the invention has a dense mesh, which means that it has protective effects on the skin. This film effect forms on the surface of the epidermis a molecular barrier capable of protecting from external (chemical or mechanical) aggressions whilst maintaining the water exchanges of the skin. Studies performed ex-vivo or in vivo have demonstrated that the agent according to the invention reduces the penetration of pollutants including PM10-type fine particles and carbon particles. It has similar effects on the penetration of allergens, irritants and heavy metals. It also limits the bacterial adhesion of *Staphylococcus aureus* to the skin. All of these effects are rapid since the shield effect can be observed from 15 minutes and up to 24 hours after application. Moreover, the biopolymer of the invention protects the barrier function of skin subjected to mechanical aggressions. A test performed in vivo shows that the twice-daily application of an agent according to the invention for 21 days reduces Insensible Water Loss (IWL) caused by a mechanical stress (=strippings).

An additional analysis also demonstrated the non-occlusive action of the agent according to the invention: in the absence of aggression, it does not alter the skin's insensible water loss.

a) Effect of the Agent According to the Invention on the Penetration of Pollutants The fine particles emitted during episodes of pollution lead to skin damage and cause the appearance of wrinkles or pigment marks. The aim of this study was to assess in vivo the protective effect of an agent according to the invention with regard to the adhesion of fine particles of air pollution with a diameter of 10 μm to the skin. These fine particles consist of different pollutants such as polyaromatic hydrocarbons (PAH), and other nitrated forms (nitro-PAH), chlorinated chemical products (PCB), pesticides, hydrocarbons and heavy metals. They are collected in urban areas.

This study was performed on 10 volunteers with healthy skin on the inner surface of the forearms and skin explants previously altered in order to mimic a human altered skin.

The alteration of the explants was achieved by stripping with cyanoacrylate adhesive. This physical method allows the superficial part of the epidermis to be peeled off, thus reducing the barrier function of the skin. The alteration was validated by measuring the transepithelial electrical resistance (TEER), which should be reduced by 80%.

The fine particles were quantified in photographs before and after applications of fine particles, as well as after their rinsing.

The agent according to the invention in aqueous solution at different concentrations (0.10%, 0.25%, 0.50% and 1.00%) was applied over a 2 cm$^2$ surface of the skin. After 20 mn, the cutaneous areas were photographed and a suspension of fine particles was applied. After 50 mn, new photographs of the areas were taken before and after standardized rinsing.

The quantity of particles having adhered to the cutaneous surface was proportional to the color of the area. The lighter the area, the fewer particles adhered.

The averages of the results for the panel of 10 volunteers are given in Table 5a and for the 16 skin explants in Table 5b TABLE 5a

|  | Adhesion of particles after rinsing (%) | % Adhesion of particles/ Control |
|---|---|---|
| Distilled water | 68 |  |
| Agent at 0.1% | 52 | −23% |
| Agent at 0.25% | 49 | −28% |
| Agent at 0.5% | 42 | −38% |
| Agent at 1.0% | 36 | −47% |

In the conditions of this study, by forming a protective film effect on the surface of the skin, the cosmetic or dermocosmetic agent according to the invention at 1% reduces the adhesion of fine particles to the skin by 47%.

TABLE 5b

|  | Adhesion of particles after rinsing (%) | % Adhesion of particles/ Control |
|---|---|---|
| Distilled water | 64 |  |
| Agent at 0.1% | 53 | −17% |
| Agent at 0.25% | 50 | −22% |
| Agent at 0.5% | 47 | −26% |
| Agent at 1.0% | 37 | −42% |

In the conditions of this study, by forming a protective film effect on the surface of the altered skin, the cosmetic or dermocosmetic agent according to the invention at 1% reduces the adhesion of fine particles to the altered skin by 42%. The cosmetic or dermocosmetic agent according to the invention therefore protects the skin from the harmful effects of pollution.

b) Effect of the Agent According to the Invention on the Penetration of Irritants The aim of this study was to demonstrate that the agent according to the invention prevents the penetration of a cutaneous irritant. The protective effect was assessed for the agent formulated at 0.50% as an emulsified gel (composition of Example 3) in the context of a "stinging test".

This test makes it possible to determine the ability of the panelist to perceive and assess the sensations engendered by the application of a lactic acid solution to the nostrils. In fact, the application of this irritant solution causes the appearance of sensations of discomfort such as tingling, burning and itching. The study was performed on 12 healthy volunteers. The effect of the emulsified gels tested on cutaneous reactivity after application of a solution of lactic acid was assessed on a 4-point numerical scale before and after application.

In the conditions of this study, the agent according to the invention formulated at 0.50% significantly reduces by 22% the sensations of discomfort caused by the application of an irritant agent. This effect was perceived by 58% of the volunteers.

By forming a protective film effect, the agent according to the invention protects sensitive skins against irritants.

c) Effect of the Agent According to the Invention on the Penetration of Allergens The aim of this study was to assess the capacity of the agent according to the invention to prevent the transcutaneous penetration of an allergen by forming a protective film on the surface of the skin. The study was performed on skin explants by using static Franz diffusion cells.

The barrier effect of the agent according to the invention was assessed by quantifying the capacity of an allergen (amyl cinnamaldehyde) formulated at 0.2% in an emulsion (composition of Example 4), to cross the cutaneous barrier ex vivo in the presence or absence of the agent according to the invention. The amyl cinnamaldehyde content was quantified by gas chromatography/mass spectrometry.

The percentage of allergen present in the skin was calculated by means of the following formula:

$$\% \text{ allergen in the skin} = 100 - \left(\frac{QM_{T24}}{QM_{ini}}\right) \times 100$$

where:
$QM_{T24}$ quantity of allergen in the formula recovered from the surface of the skin at t=24 hours.
$QM_{ini}$: quantity of allergen in the formula deposited on the surface of the skin.

The quantities of allergen present in the skin after 24 hours are given in Table 6.

TABLE 6

|  | % of Allergen in the skin | Variation compared to the control |
|---|---|---|
| Control | 33.9 |  |
| Agent at 1.00% | 14.4 | −62% |

In the conditions of the study, by forming a protective film on the surface of the skin, the agent according to the invention, at 1.00%, reduces the transcutaneous penetration of amyl cinnamaldehyde by 62%.

d) Effect of the Agent According to the Invention on the Penetration of Heavy Metals The aim of this study was to assess ex vivo the capacity of the agent according to the invention to prevent the transcutaneous penetration of heavy metals by forming a protective film on the surface of the skin. The study was performed after depositing cadmium on the surface of the skin by using static Franz diffusion cells. The amount of heavy metals having penetrated was quantified by plasma source optical emission spectrometry (ICP-OES).

The agent according to the invention was deposited at 0.5% on the surface of the skin. After several hours, a deposit of 4 ppm of cadmium was made on the explants. After 14 h, the cadmium on the surface of the explant was recovered with the aid of a strip. The cadmium contained in the different samples was extracted in a solution of nitric acid. All of these samples were measured by ICP-OES. The results are given in Table 7.

TABLE 7

|  | % of Cadmium in the skin | Variation compared to the control |
|---|---|---|
| Control | 69.1 |  |
| Agent at 1.00% | 40.7 | −41% |

In the conditions of the study, the agent according to the invention, at 0.5%, reduced the transcutaneous penetration of cadmium by 41% in healthy skin. By forming a protective film on the surface of the skin, it protects it against the harmful effects of heavy metals present in pollution.

e) Effect of the Agent According to the Invention on the Bacterial Adhesion of *Staphylococcus aureus* to the Skin The aim of this study was to assess in vitro the capacity of the agent according to the invention to prevent the formation of a biofilm by the *Staphylococcus aureus* (SA) bacterium. This bacterium is a pathogenic bacterium present in an abnormally high quantity in various skin disorders. By adhering to the surface of the skin, it forms a biofilm that upsets the homeostasis of the skin.

This study was performed on reconstructed epidermises after application of a solution of *Staphylococcus aureus*. The adhesion and colonization by this bacterium was revealed by a scanning electron microscope (SEM).

The reconstructed epidermises were treated topically with the agent according to the invention at 0.5%. After 24 h, they were treated topically with a solution of SA and incubated for 24 h. The biofilm was then visually examined.

Figure 6A:
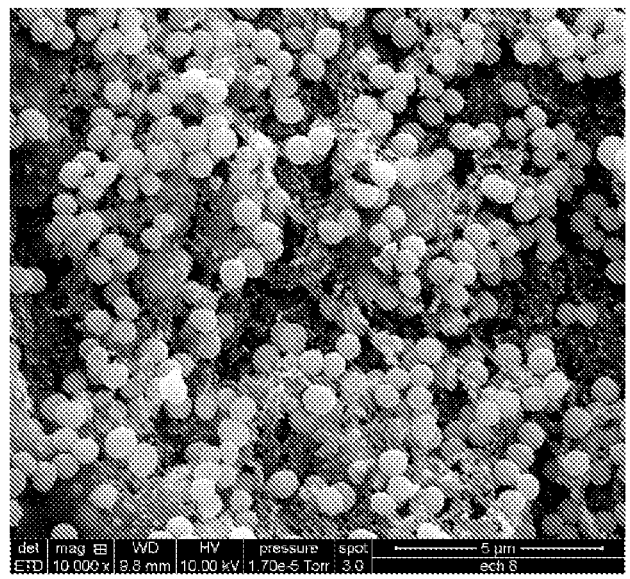
FIG. 6A represents the biofilm of *Staphylococcus aureus* on the control reconstructed epidermis.
Figure 6B:
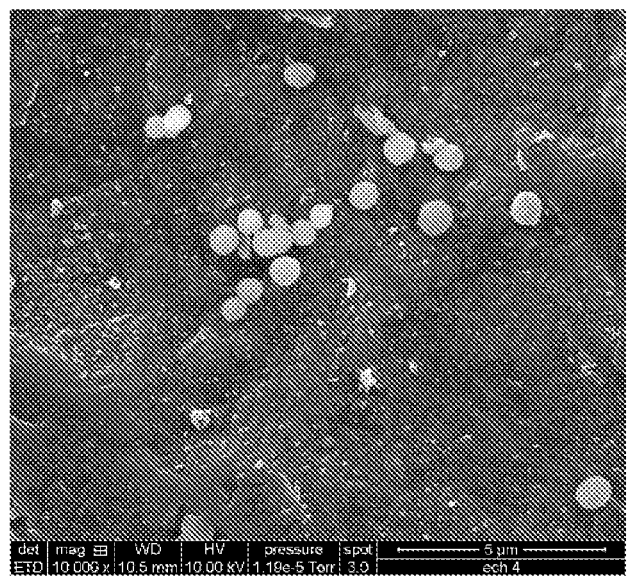
FIG. 6B represents the biofilm of *Staphylococcus aureus* on the reconstructed epidermis treated with the agent according to the invention.

FIG. 6A represents the biofilm of SA on the control reconstructed epidermis and FIG. 6B on the reconstructed epidermis treated with the agent according to the invention.

Tested at 0.5% on reconstructed epidermises, the agent according to the invention limits the adhesion of *Staphylococcus aureus* and consequently the formation of biofilm.

f) Effect of the Agent According to the Invention on the Cutaneous Barrier

The aim of the study was to assess, in vitro, the capacity of the agent according to the invention formulated at 0.50% as an emulsified gel (composition as described in the Examples section), to preserve the barrier function subjected to a mechanical aggression (5 strippings).

This study was performed on 11 healthy volunteers. The insensible water loss was measured with the aid of a Tewameter® TM300 probe (Courage and Khazaka).

The results are given in Table 8.

TABLE 8

|  | IWL (g/h/m$^2$) | | Variation/Placebo (%) |
|---|---|---|---|
|  | Before aggression | After aggression |  |
| Placebo | 5.8 | 7.6 |  |
| Agent at 0.50% | 5.9 | 6.9 | −14 |

In the conditions of this study, in comparison to the placebo, the agent according to the invention formulated at 0.50% significantly limits by 14% the insensible water loss caused by mechanical aggression.

By forming a protective film effect, the agent according to the invention makes it possible to reinforce the cutaneous barrier against a mechanical aggression.

2) Lifting Film Effect

Numerous analyses were conducted in vivo demonstrating the multifunctionality of the agent according to the invention. It was shown to be a powerful lifting agent capable of:

smoothing the skin in two areas of the body (forearm and stomach);

improving the biomechanical properties of the skin;

reducing wrinkles at the crow's feet and around the lips.

These studies made it possible to measure the influence of various parameters: the dose of the agent, the duration of the treatment and the impact of the formulation. Efficacy was quantified instrumentally or assessed by the volunteers themselves.

Thus, it was shown that in the short term, the agent according to the invention has a strong and dose-dependent tensor effect. This effect, visible after 30 minutes, remains significant after two hours. It smooths the skin on the forearm and stomach and also immediately reduces wrinkles at the crow's feet or around the lips.

In the long term: the agent according to the invention demonstrates its anti-wrinkle efficacy since, after 7 days of treatment, it enables visible filling of wrinkles around the lips. The smoothing effect on the stomach lasts for up to 14 days.

Thus, the agent according to the invention has lifting properties. It enables an improvement of the cutaneous microrelief in different areas of the body and the erasure of facial wrinkles. It can therefore be incorporated into lifting and anti-ageing treatments.

a) Smoothing Effect of the Agent According to the Invention on the Cutaneous Microrelief The smoothing effect of the agent according to the invention on the cutaneous microrelief was assessed in two areas: the forearms and the stomach.

The aim of the first study was to assess, in vivo and placebo-controlled, the smoothing effect on the forearms of the agent according to the invention, formulated at different doses (0.05%, 0.10%, 0.25% and 0.50%) in an emulsified gel (composition of Example 3), 30 minutes and 2 hours after an isolated application.

The aim of the second study was to assess, in vivo and placebo-controlled, the smoothing effect of the agent according to the invention, formulated at 0.10% as an emulsified gel (composition of Example 3) on the stomach after 1 hour and 14 days of twice-daily applications. The smoothing effect was measured by fringe projection (Eotech system) after making imprints. The characteristic parameters of the roughness of the skin's microrelief (Sa and Sq) were assessed.

The results are given in Tables 9 and 10.

TABLE 9

|  | Variation/Placebo (%) | | | |
|---|---|---|---|---|
|  | 30 minutes | | 2 hours | |
|  | Sa Parameter | Sq Parameter | Sa Parameter | Sq Parameter |
| Agent at 0.05% | −4.1% | −4.1% | −4.0% | −4.4% |
| Agent at 0.10% | −4.8% | −4.5% | −4.7% | −4.7% |
| Agent at 0.25% | −6.1% | −5.4% | −5.0% | −4.9% |
| Agent at 0.50% | −6.8% | −6.7% | −5.4% | −5.5% |

TABLE 10

| | Variation/Placebo (%) | | | |
| --- | --- | --- | --- | --- |
| | 1 hour | | 14 days | |
| | Sa Parameter | Sq Parameter | Sa Parameter | Sq Parameter |
| Agent at 0.10% | −8.6% | −9.6% | −9.0% | −9.8% |

In the conditions of these studies, the agent according to the invention has a significant tensor effect on the microrelief of the forearms, after 30 minutes at the dose of 0.10% and was at its maximum at 0.50%. This effect lasts two hours after the application.

Just 1 hour after application, the agent according to the invention formulated at 0.10% tends to smooth the cutaneous microrelief on the stomach by reducing the 3D roughness parameters.

After 14 days of twice-daily applications, the agent according to the invention smooths the microrelief by significantly reducing: the Sa parameter by 9.0% and the Sq parameter by 9.8%. This effect was observed in 89% and 83% respectively of the volunteers tested.

The agent according to the invention therefore has a smoothing effect on the cutaneous microrelief, this effect being dose-dependent.

b) Effect of the Agent According to the Invention on Wrinkles

The aim of this study was to assess, in vivo and placebo-controlled, the anti-wrinkle effect of the agent according to the invention formulated in three types of cosmetic formulas:

as an emulsified gel (composition of Example 3) at different doses (0.10% and 0.50%), 30 minutes and 2 hours after a single application to the crow's foot;

as a serum (composition of Example 5) at 1.00%, 30 minutes after a single application to the crow's foot;

as a cream mask (composition of Example 7) at 0.5%, 30 minutes after a single application to facial wrinkles and after applying 2 cream masks over a period of 7 days.

In the case of the emulsified gel, the anti-wrinkle effect was measured by means of fringe-projection analysis (Eotech system) at the crow's foot and blind clinical assessment of photographs by experts on a scoring scale of 1 to 6 and based on the assessment of the depth of the deepest wrinkle.

In the case of the serum, the anti-wrinkle effect was assessed clinically by experts on the basis of photographs and scored by the volunteers themselves. In the case of the cream mask, the anti-wrinkle effect was measured by means of fringe-projection analysis of the wrinkles above the lips.

Immediate Anti-Wrinkle Effect of the Agent According to the Invention Formulated as an Emulsified Gel by Fringe-Projection:

The results corresponding to the anti-wrinkle effect of the agent according to the invention formulated at 0.10% and 0.50% as emulsified gel (composition of Example 3), 30 minutes and 2 hours after a single application, are shown in Table 11.

TABLE 11

| | Variation/Placebo (%) | | | |
| --- | --- | --- | --- | --- |
| | 30 minutes | | 2 hours | |
| | Agent at 0.10% | Agent at 0.50% | Agent at 0.10% | Agent at 0.50% |
| Sa Parameter | −4.9% | −5.2% | −5.2% | −6.2% |
| Sq Parameter | −5.0% | −5.0% | −6.6% | −6.9% |
| Negative Volume | −11.5% | −12.3% | −18.3% | −21.2% |

In the conditions of this study, the agent according to the invention formulated as an emulsified gel has a significant immediate anti-wrinkle effect on the crow's foot after 30 minutes. This effect lasts for two hours after application and is dose-dependent. It significantly reduces the characteristic parameters of the cutaneous relief of the crow's foot. This effect is seen for the dose of:

0.10%: for 68% of the volunteers 30 minutes after application, for 67% of the volunteers 2 hours after application;

0.50%: for 70% of the volunteers 30 minutes after application, for 74% of the volunteers 2 hours after application.

Immediate Anti-Wrinkle Effect of the Agent According to the Invention Formulated as an Emulsified Gel, as Shown in Photographs The results corresponding to the effect of the agent according to the invention, formulated as an emulsified gel (composition as described in the Examples section) at different doses, on the crow's feet wrinkle stage, 30 minutes and 2 hours after a single application, are given in Table 12.

TABLE 12

| | Variation/Placebo (%) | |
| --- | --- | --- |
| | 30 minutes | 2 hours |
| Agent at 0.10% | −6.8% | −8.7% |
| Agent at 0.50% | −7.9% | −12.1% |

In the conditions of this study, the agent according to the invention formulated as an emulsified gel significantly reduces the crow's feet wrinkle stage after 30 minutes. This effect lasts for two hours after application and is dose-dependent. Two hours after applying the agent according to the invention at 0.10%, the panel of experts noticed an improvement in the crow's feet wrinkle stage in 55% of cases. This percentage reached 63% when the agent is used at 0.50%.

Immediate Anti-Wrinkle Effect, Assessed on the Basis of Photographs, of the Agent According to the Invention Formulated as a Serum The results corresponding to the effect of the agent according to the invention, formulated as a serum (composition as described in the Examples section) at 1%, on the crow's feet wrinkle stage, 30 minutes after a single application are given in Table 13.

TABLE 13

| | Variation/D0 (%) | Variation/Placebo (%) |
| --- | --- | --- |
| Placebo | +1.0% | |
| Agent at 100% | −9.7% | −10.7% |

In the conditions of this study, 30 minutes after a single application, the agent according to the invention formulated at 1.00% in a serum, significantly reduces by 10.7% the average crow's feet wrinkle stage in 60% of the volunteers.

Due to its rapid action, it thus gives the skin an express lifting effect.

In the conditions of this study and only 30 minutes after a single application over the entire face, the agent according to the invention formulated at 1.00% in a serum reduces the average wrinkle stage of the volunteers.

This effect is perceived by the volunteers themselves who are more numerous in the group that tested the agent according to the invention in finding that the agent has an immediate tensor effect, makes the skin firmer and more luminous.

Anti-Wrinkle Effect by Fringe-Projection of the Agent According to the Invention Formulated as a Cream Mask The results corresponding to the effect of the agent according to the invention, formulated at 0.50% as a cream mask (composition as described in the Examples section), on wrinkles above the lips are given in Table 14.

TABLE 14

|  | Variation/Placebo (%) | |
| --- | --- | --- |
|  | After 1 application | After 3 applications |
| Sa Parameter | −2.1% | −4.6% |
| Sq Parameter | −2.9% | −4.6% |
| Negative Volume | −10.7% | −11.9% |

In the conditions of this study, the agent according to the invention formulated at 0.5% as a cream mask reduced the characteristic parameters of wrinkles above the lips. This effect is visible from the first application in 80% of volunteers (−10.7%). After three applications, the efficacy of the agent increases (−11.9%) and is observed in 65% of volunteers.

The formula containing the agent is perceived overall as being more effective than the placebo formula by the volunteers who tested it.

From the first application, more than 90% of the subjects experienced an immediate tensor effect and found their skin to be smoother and more luminous.

After 3 applications, all of the subjects found their skin to be more hydrated. They saw that their skin was smoother and softer and the wrinkles and fine lines were less visible.

c) Effect of the Agent According to the Invention on Skin Surface Properties

The aim of this study was to assess, in vivo and placebo-controlled, the tensor effect of the agent according to the invention, formulated at different doses (0.05%, 0.10%, 0.25% and 0.50%) in an emulsified gel (composition of Example 3), 30 minutes and 2 hours after an isolated application.

The tensor effect was measured using a Cutometer® Dual MPA 580 (Courage & Khazaka). The results corresponding to this tensor effect are given in Table 15.

TABLE 15

|  | Variation/Placebo (%) | | | |
| --- | --- | --- | --- | --- |
|  | 30 minutes | | 2 hours | |
|  | -Uf Parameter | -Ue Parameter | -Uf Parameter | -Ue Parameter |
| Agent at 0.05% | +3.2% | +4.4% | +5.1% | +5.7% |
| Agent at 0.10% | +3.7% | +6.0% | +5.5% | +6.1% |
| Agent at 0.25% | +4.1% | +6.0% | +6.3% | +7.0% |
| Agent at 0.50% | +6.2% | +9.2% | +7.2% | +10.0% |

In the conditions of this study and in comparison to the placebo, the agent according to the invention has a significant tensor effect 30 minutes after the 0.05% dose and is dose-dependent. This effect lasts for two hours after application.

3) Perceptible Film Effect

The sensations perceived by the users on the application of the agent according to the invention were analyzed.

Sensory experts concluded that the product had a significant and dose-dependent tensor effect. This effect was perceived in different formulas (gel or foundation). In parallel, some non-expert volunteers also perceived tensor effects immediately and 30 minutes after applying the agent to the face.

The visual effects of the agent according to the invention were also measured. It was thus shown that its application improves the overall appearance of the face, manifested by a reduction in pore surface and an increase in the radiance of the complexion. Self-assessments in front of a mirror showed that the volunteers considered their skin to be smoother, more luminous, firm and hydrated. Lastly, incorporated in a foundation formula, the agent increases the hold of make-up.

The lifting effect was perceived by sensory experts and non-experts. The invention enables an overall improvement in the appearance of the volunteers' faces by reducing the size of pores and giving the skin a radiance boost.

a) Sensory Tensor Effect of the Agent According to the Invention

The aim of this study was to quantify, in vivo and placebo-controlled:
- on a panel of sensory experts, the tensor and smoothing effects perceived after application of the agent according to the invention formulated at 0.50% in a foundation (composition of Example 6);
- on a panel of sensory experts, the tensor effect perceived after application of the agent according to the invention formulated at different doses as a gel (composition of Example 4);
- on a panel of non-experts, the tensor and smoothing effects perceived after application of the agent according to the invention formulated at 0.10% or 0.50% as an emulsified gel (composition of Example 3).

The perception of these effects was assessed on a score of 1 to 10 (1: no sensation, 10: maximum tensor sensation).

The foundation was applied by light massage over the entire face. The score was given immediately, 5 mn and 15 mn after application, based on the sensations felt and the self-observations made in the mirror in controlled lighting.

The gel was applied by light massage into the crow's foot. The score was given 3 mn, 5 mn and 10 mn after application of the product.

The emulsified gel was applied by light massage over the entire face. The tensor and smoothing effects were measured immediately, 5, 15 and 30 minutes after application of the product.

The results obtained are given in Tables 16 to 18.

TABLE 16

| Foundation | Score Average (U.A.) | |
|---|---|---|
| | Tensor Effect | Smoothing Effect |
| Placebo | 0.8 | 0.7 |
| Agent at 0.50% | 1.7 | 1.4 |

In the conditions of this study, after one application, the agent at 0.5% in a foundation had significantly greater tensor and smoothing effects than those of the placebo.

TABLE 17

| Gel | Average Score (UA) |
|---|---|
| Placebo | 1.8 |
| Agent at 0.05% | 2.4 |
| Agent at 0.10% | 3.5 |
| Agent at 0.25% | 4.2 |
| Agent at 0.50% | 5.1 |

After application of the agent according to the invention formulated as a gel at different doses on the crow's foot area:
after the 0.10% dose, 83% of the sensory experts trained to perceive and quantify the sensation of the tensor effect felt a tensor effect greater than the average effect felt with the placebo formula,
at the 0.50% dose, this figure rose to 98%.

TABLE 18

| Emulsified Gel | Average Score (U.A.) | |
|---|---|---|
| | Tensor Effect | Smoothing Effect |
| Placebo | 2.5 | 3.6 |
| Agent at 0.10% | 3.6 | 4.6 |
| Agent at 0.50% | 3.8 | 4.9 |

In the conditions of this study, after a single application, the agent according to the invention formulated at 0.10% or 0.50% as an emulsified gel, was significantly better perceived than the placebo formula by the non-expert sensory volunteers. In fact, it was experienced as having a tensor and smoothing effect by these volunteers, this effect being dose-dependent.

b) Effect of the Agent According to the Invention on the Overall Appearance of the Face The aim of this study was to assess, in vivo and placebo-controlled, the effect of the agent according to the invention formulated at 0.50% as a cream mask (composition of Example 8), on the overall improvement of the face, 30 minutes after 1 application or after a treatment of 3 masks applied over 7 days.

The overall improvement of the face was assessed by means of:
a study of the pore surface on the check by fringe projection (Eotech system);
a visual assessment of the radiance of the complexion by experts;
a self-assessment of the performance perceived by the volunteer via a questionnaire completed after observation in front of a mirror.

Cream masks (placebo or agent according to the invention) were applied in a thick layer over the entire face. The volunteers had to leave it to act for 20 minutes before massaging in the excess with the fingertips.

The results on the pore surface corresponding to the effect of the agent, formulated at 0.50% as a cream mask, compared to a placebo group are given in Table 19.

TABLE 19

| | Variation/Placebo (%) |
|---|---|
| After 1 application | −9.2% |
| After 3 applications | −10.4% |

In the conditions of this study, from the first use, the agent according to the invention formulated at 0.50% in a cream mask significantly improved the skin texture by reducing the pore surface by 9.2% (effect observed in 65% of subjects).

This reduction increased 10.4% after 3 applications of cream mask. This effect was observed in 70% of the volunteers who tested the formula containing the agent, against only 38% for those who tested the placebo.

Thus, the agent according to the invention helps in the overall improvement of the face by refining the skin texture.

The results on the radiance of the complexion assessed by the experts corresponding to the effect of the agent according to the invention, formulated at 0.50% as a cream mask, in comparison to a placebo group, are given in Table 20.

TABLE 20

| | Variation/Placebo (%) | |
|---|---|---|
| | After 1 application | After 3 applications |
| Radiance | +5.9% | +6.5% |
| Eye Fatigue | −7.0% | −14.1% |
| Skin Texture | +5.9% | +7.1% |

The agent according to the invention significantly improved the radiance of the complexion. From the first application, the radiance of the skin was increased, the state of eye fatigue diminished and the skin texture was refined.

The results of the performance perceived, based on the close-ended questions of the visual self-assessment in front of a mirror, are given in Table 21.

TABLE 21

| | After 1 application | | After 3 applications | |
|---|---|---|---|---|
| Total of "tend to agree" and "agree" answers (%) | Placebo Group | Agent at 0.50% Group | Placebo Group | Agent at 0.50% Group |
| This treatment has an immediate tensor effect. | 62 | 91 | 57 | 87 |
| This treatment hydrates the skin well. | 90 | 100 | 90 | 100 |
| With this treatment, the skin is smooth. | 81 | 91 | 76 | 87 |
| With this treatment, the skin is more luminous. | 62 | 91 | 76 | 83 |
| With this treatment, the skin is visibly firmer. | 57 | 78 | 62 | 83 |
| This treatment leaves the skin feeling comfortable. | 90 | 96 | 8 | 100 |

The formula containing the agent according to the invention was perceived overall as being more effective than the placebo formula by the volunteers who tested it.

From the first application, 91% of subjects experienced an immediate tensor effect and found their skin to be smoother and more luminous.

After 3 applications of the cream mask formula, all of the subjects who tested the agent according to the invention found their skin to be more hydrated and comfortable. They also observed that their skin was smoother and visibly firmer.

c) Effect of the Agent According to the Invention on Make-Up Hold

The aim of this study was to assess, in vivo and placebo-controlled, the influence of the agent according to the invention formulated at 0.50% on the hold over time of a foundation (composition of Example 6).

The hold of the foundation was quantified in digital photographs.

The agent formulated as a foundation was applied in the morning in real conditions of use, at home by the volunteers. Immediately after application then at the end of the day (on average 11 hours after application), the volunteers completed a self-assessment questionnaire.

The results corresponding to the loss of color intensity of a foundation under the effect of the agent according to the invention formulated at 0.50% over time in comparison to a placebo are given in Table 22.

TABLE 22

| | Loss of color intensity (%) | | |
| --- | --- | --- | --- |
| | 2 hours | 4 hours | 6 hours |
| Placebo | 10% | 15% | 24% |
| Agent at 0.50% | 5% | 11% | 18% |

In the conditions of this study, the agent according to the invention formulated at 0.50% in a foundation significantly prolonged the make-up hold compared to the placebo formula (+33% more time). This effect was observed in 63% of the volunteers.

In these conditions of use, the agent formulated at 0.50% in a foundation was better perceived overall by the users, who preferred it to the placebo foundation.

d) Effect of the Agent According to the Invention on the Dispersion of Pigments

The aim of this study was to show the effect of the agent according to the invention on the dispersion of pigments. For this, two types of pigments usually present in make-up products were tested: lipophilic and hydrophilic pigments. In test tubes, 2 g of lipophilic (OTW-2 Yellow LL) or hydrophilic (Red iron oxide) pigment were added to distilled water or to 0.5% or 1% solutions of the agent according to the invention. Photographs were taken immediately after agitation and after at least 1 hour at rest. The results are qualitative and were assessed according to 4 levels of pigment dispersion:

| | |
| --- | --- |
| No dispersion | − |
| Poor dispersion | + |
| Good dispersion | ++ |
| Very good dispersion | +++ |

The results were as follows:

TABLE 23

| | Lipophilic pigment | |
| --- | --- | --- |
| | Dispersion at T0 | Dispersion at T1h |
| Water control | +++ | − |
| Agent according to the invention at 0.5% | +++ | ++ |
| Agent according to the invention at 1% | +++ | ++ |

TABLE 24

| | Lipophilic pigment | |
| --- | --- | --- |
| | Dispersion at T0 | Dispersion at T1h |
| Water control | +++ | − |
| Agent according to the invention at 0.5% | +++ | ++ |
| Agent according to the invention at 1% | +++ | ++ |

In the conditions of the study, the agent according to the invention at 0.5% and 1% had pigment-dispersion properties.

Thus, it helps to stabilize the formulas and encourage a homogenous distribution of the pigments on the surface of the skin.

4) "Beauty Booster" Second-Skin Film Effect

Tests aimed at showing that faces treated with the agent according to the invention were perceived by third parties as more attractive or less wrinkled were also conducted.

Thus, the lay assessors judged that:

in 53% of cases, the agent according to the invention increases the attractiveness of the face of young volunteers, in 55% of cases, the agent according to the invention reduces facial wrinkles in mature people.

We have also performed two consumer tests in France and Asia. The Caucasian volunteers applied the agent according to the invention as emulsified gel twice daily for 14 days. The Asian volunteers performed a treatment based on 6 applications of a cloth mask for a period of 15 days.

These two studies revealed that the treatment with the agent according to the invention received a systematically higher score than the placebo. The Caucasian volunteers said that their skin was toned, firmer like lifted with more clearly defined facial contours and a remodeled oval shape of the face. According to the comments of the Asian volunteers, their complexion was more radiant and luminous and their skin was toned and softer.

The efficacy of the agent according to the invention was confirmed by the users themselves as well as by third parties. This filmogenic agent acts as a real beauty activator by improving the attractiveness of the faces of the young and the wrinkled appearance of mature skins.

In summary, the agent according to the invention was tested on two types of skin (Caucasian and Asian), after 14 analysis times (instantaneous, medium-term, long-term) for 5 doses (0.05% to 1%) and in 7 different cosmetic formulas (emulsion, emulsified gel, gel, serum, foundation, cream mask and cloth mask).

a) Effect of the Agent According to the Invention on Attractiveness as Perceived by a Third Party The aim of this study was to assess, in vivo, the effect of the agent according to the invention formulated at 0.50% as a cream mask (composition of Example 8), on the overall improvement of the face perceived by lay assessors.

The attractiveness of the face was scored on the basis of digital photographs. The cream masks (placebo or agent according to the invention) were applied in a thick layer over the entire face. The volunteers had to leave it to act for 20 minutes before massaging in the excess with the fingertips.

The panels comprised one panel of young skins (44 healthy volunteers of an average age of 40) and one panel of mature skins (40 healthy volunteers of an average age of 62).

The results corresponding to the effect of the agent according to the invention formulated at 0.50% as a cream mask on the attractiveness of the face in the young panel are given in Table 25, and on the wrinkles of the mature panel in Table 26.

TABLE 25

| | Assessors (%) | | | |
|---|---|---|---|---|
| | Placebo | | Agent at 0.50% | |
| | After 1 application | After 3 applications | After 1 application | After 3 applications |
| Observed an improvement | 14 | 25 | 24 | 53 |
| Observed no improvement | 86 | 75 | 76 | 47 |

In the conditions of this study, after three applications of a cream mask containing 0.50% of the agent according to the invention, the lay assessors observed an improvement in the appearance of the face in 53% of cases against only 25% of cases for subjects who tested the placebo formula.

TABLE 26

| | Assessors (%) | | | |
|---|---|---|---|---|
| | Placebo | | Agent at 0.50% | |
| | After 1 application | After 3 applications | After 1 application | After 3 applications |
| Observed an improvement | 15 | 25 | 20 | 45 |
| Observed no improvement | 85 | 75 | 80 | 55 |

In the conditions of this study, after three applications of a cream mask containing 0.50% of the agent according to the invention, the lay assessors observed a reduction in facial wrinkles in 45% of cases against only 25% in cases of subjects who tested the placebo formula.

The agent according to the invention formulated at 0.50% as a cream mask thus visibly reduces facial wrinkles.

b) Consumer Studies of the Agent According to the Invention

Two consumer studies were conducted to show the effect of the agent according to the invention; one study on French consumers and one study on Asian consumers.

The aim of the French consumer study was to compare the efficacy of a treatment containing the agent according to the invention formulated at 0.50% as an emulsified gel (composition of Example 3) with its placebo.

136 women living in France, aged between 40 and 55, having all facial skin types with no sensitivity quota, saying that they had wrinkles and/or fine lines as well as a dull complexion, lacking radiance and users of firming treatments. 68 women used the placebo and 68 women the agent according to the invention.

The sensations observed during the treatment were assessed by means of self-assessment questionnaires completed at home. The assessments were made 30 minutes after a first application and on the 8th and 15th day of testing. The panelists applied the treatment over the entire face, on perfectly clean skin, twice a day, morning and evening, for 14 days, instead of their usual facial treatment. The results of the close-ended questions after the first application are given in Table 27.

TABLE 27

| | After 1 application | |
|---|---|---|
| | Placebo | Agent at 0.50% |
| This treatment tones the skin | 41 | 59 |
| This treatment makes the skin firmer | 35 | 49 |
| With this treatment, the skin is tighter | 41 | 54 |
| This treatment has an immediate tensor effect | 43 | 54 |
| With this treatment, the skin is softer | 77 | 87 |
| With this treatment, the skin is luminous | 44 | 49 |
| With this treatment, my pores are tightened | 34 | 38 |
| This treatment minimizes imperfections | 27 | 31 |

The result of the close-ended questions after 7 days of twice-daily applications are given in Table 28.

TABLE 28

| | After 7 days of application | |
|---|---|---|
| | Placebo | Agent at 0.50% |
| This treatment tones the skin | 63 | 73 |
| This treatment makes the skin firmer | 69 | 70 |
| With this treatment, the skin is tighter | 61 | 69 |
| This treatment has a tensor effect | 69 | 75 |
| With this treatment, the skin is softer | 79 | 88 |
| With this treatment, the skin is luminous | 58 | 64 |
| This treatment minimizes imperfections | 48 | 60 |
| With this treatment, the contours of the face appear more clearly defined | 36 | 49 |
| With this treatment, the oval shape of the face is remodeled | 24 | 39 |

The results of the close-ended questions after 14 days of twice-daily applications are given in Table 29.

TABLE 29

| | After 14 days of application | |
|---|---|---|
| | Placebo | Agent at 0.50% |
| This treatment tones the skin | 67 | 76 |
| This treatment makes the skin firmer | 76 | 84 |
| With this treatment, the skin is visibly tighter | 63 | 73 |
| This treatment has a tensor effect | 72 | 78 |
| With this treatment, the skin is like lifted | 54 | 63 |
| With this treatment, the skin is softer | 85 | 93 |
| With this treatment, the skin is luminous | 64 | 72 |
| This treatment minimizes imperfections | 55 | 58 |
| With this treatment, the contours of the face appear more clearly defined | 48 | 63 |
| With this treatment, the oval shape of the face is remodeled | 34 | 58 |

The results of the open comments after 14 days of twice-daily applications are given in Table 30.

TABLE 30

| Open comments | After 14 days of application | |
|---|---|---|
| | Placebo | Agent at 0.50% |
| Immediate smoothing effect, skin is smooth, less wrinkled | 9 | 16 |
| Skin more luminous, less dull, radiant | 16 | 22 |
| Pores tightened, finer skin texture | 7 | 12 |
| Immediate tensor effect | 16 | 19 |
| Skin firmer (*) | 2 | 10 |
| Skin more beautiful, improved | 9 | 16 |

Overall, in the conditions of this study, the women who used the formula containing the agent according to the invention attributed better results for each item than those who tested the placebo formula.

Significantly more volunteers found their skin to be more toned, firmer, like lifted and with more clearly defined facial contours and a remodeled oval of the face.

The aim of the Asian consumer test was to compare the efficacy of a cloth mask (composition described in the Examples section) containing the agent according to the invention formulated at 0.50% with a placebo formula.

134 Asian women, aged between 30 and 50 living in Singapore, having all facial skin types with no sensitivity quota, saying that they had wrinkles and/or fine lines as well as a dull complexion, lacking radiance and users of masks intended for facial treatment. 66 women tested the agent according to the invention and 68 women tested the placebo.

The sensations observed during the treatment were assessed by means of self-assessment questionnaires completed at home. The assessments were made after application of the first mask and after application of 5 other masks. The masks were applied on D0, D3, D6, D9, D12 and D15. The results of the close-ended questions after 1 application are given in Table 31.

TABLE 31

| | After 1 application | |
|---|---|---|
| | Placebo | Agent at 0.50% |
| This treatment hydrates the skin well | 46 | 61 |
| This treatment leaves the skin soft | 44 | 68 |
| This treatment tones the skin | 40 | 47 |
| With this treatment, the skin is luminous | 34 | 38 |
| With this treatment, the skin is vitalized | 38 | 45 |
| With this treatment, the complexion is radiant | 40 | 44 |
| With this treatment, my pores are tightened | 32 | 41 |
| With this treatment, the skin is smooth | 49 | 59 |
| This treatment has an immediate tensor effect | 56 | 62 |
| With this treatment, the skin is visibly tighter | 38 | 42 |

The results of the close-ended questions after 6 applications are given in Table 32.

TABLE 32

| | After 6 applications | |
|---|---|---|
| | Placebo | Agent at 0.50% |
| This treatment hydrates the skin well | 70 | 79 |
| This treatment leaves the skin soft | 71 | 86 |
| This treatment tones the skin | 64 | 80 |
| With this treatment, the skin is luminous | 64 | 74 |
| With this treatment, the skin is vitalized | 68 | 80 |
| With this treatment, the complexion is radiant | 62 | 77 |
| With this treatment, my pores are tightened | 65 | 73 |
| With this treatment, the wrinkles and fine lines are reduced | 56 | 61 |
| With this treatment, the skin is visibly tighter | 65 | 70 |

Overall, in the conditions of this study, the women who used the masks soaked with the lotion containing the agent according to the invention gave better results for each item than those who tested the placebo formula.

Significantly more volunteers found their complexion to be more radiant and more luminous and their skin to be more toned and softer.

The invention claimed is:

1. A cosmetic or dermocosmetic agent consisting of galactomannans obtained from *Caesalpinia spinosa* with average molar masses of between 5 and 30 kDa, and cross-linked sulfated galactans obtained from *Kappaphycus alvarezii* with molar masses of between 5 and 25 kDa and cross-linked with an ionic cross-linking agent, wherein the galactomannans and cross-linked sulfated galactans are present in an amount effective to produce a film-forming effect ensuring a tensor effect reducing the skin pores and reducing wrinkles and fine lines, and a skin-protector effect.

2. The cosmetic or dermocosmetic agent according to claim 1, characterized in that the galactomannans obtained from *Caesalpinia spinosa* have an average molar mass of between 8 and 25 kDa, and the cross-linked sulfated galactans obtained from *Kappaphycus alvarezii* have an average molar mass of between 8 and 20 kDa.

3. The cosmetic or dermocosmetic agent according to claim 1, characterized in that the galactomannans are obtained by hydrolysis of galactomannans of *Caesalpinia spinosa*.

4. The cosmetic or dermocosmetic agent according to claim 1, characterized in that the cross-linked sulfated galactans are obtained by hydrolysis of sulfated galactans of *Kappaphycus alvarezii*.

5. The cosmetic or dermocosmetic agent according to claim 1, characterized in that it consists of:
   60 to 90% galactomannans, and
   10 to 40% cross-linked sulfated galactans,
   the percentages being given as mass/mass.

6. The cosmetic or dermocosmetic agent according to claim 1, characterized in that it consists of:
   70 to 90% galactomannans, and
   10 to 30% cross-linked sulfated galactans,
   the percentages being given as mass/mass.

7. The cosmetic or dermocosmetic agent according to claim 1, characterized in that the galactomannans and cross-linked sulfated galactans together form an interpenetrated network.

8. A cosmetic or dermocosmetic composition suitable for a topical application onto human skin and comprising at least 0.1% of the agent according to claim 1.

9. A cosmetic or dermocosmetic method for improving a condition of skin, the method comprising applying onto the skin the cosmetic composition of claim 8.

10. The cosmetic or dermocosmetic method according to claim 9, wherein the application of the agent improves the radiance of the skin.

11. The cosmetic or dermocosmetic method according to claim 10, wherein the application of the agent combats skin ageing.

12. A method for tensing skin and/or forming a film on skin, the method comprising applying on the skin the cosmetic or dermocosmetic agent of claim 1, and thereby tensing the skin and/or forming the film on the skin.

13. A method for protecting skin, the method comprising applying on the skin the cosmetic or dermocosmetic agent of claim 1, and thereby protecting the skin.

14. A method for protecting skin against penetration of toxic molecules, the method comprising applying on the skin the cosmetic or dermocosmetic agent of claim 1, and thereby protecting the skin against the penetration of toxic molecules.

15. A method for protecting skin against bacterial adhesion of pathogens, the method comprising applying on the skin the cosmetic or dermocosmetic agent of claim 1, and thereby protecting the skin against the penetration of toxic molecules.

16. A method for improving a barrier effect of skin, the method comprising applying on the skin the cosmetic or dermocosmetic agent of claim 1, and thereby improving the barrier effect of the skin.

17. A method for improving radiance of skin and/or smoothing a microrelief of skin and/or smoothing wrinkles, the method comprising applying on the skin the cosmetic or dermocosmetic agent of claim 1, and thereby improving the radiance of the skin.

18. A method for combating skin ageing, the method comprising applying on the skin the cosmetic or dermocosmetic agent of claim 1, and thereby combating skin ageing.

19. A method for improving a make-up hold and/or improving dispersion of pigments in cosmetic formulations, the method comprising applying on the skin the cosmetic or dermocosmetic agent of claim 1, and thereby improving the make-up hold and/or improving the dispersion of pigments in cosmetic formulations.

20. A method for producing a second skin and producing a beauty booster effect, the method comprising applying on the skin the cosmetic or dermocosmetic agent of claim 1, and thereby producing the second skin and producing the beauty booster effect.

* * * * *